US009062123B2

(12) United States Patent
Dupuis et al.

(10) Patent No.: US 9,062,123 B2
(45) Date of Patent: *Jun. 23, 2015

(54) LABELLED ADRENOMEDULLIN DERIVATIVES AND THEIR USE FOR IMAGING AND THERAPY

(75) Inventors: Jocelyn Dupuis, Repentigny (CA); Alain Fournier, Pierrefonds (CA)

(73) Assignee: PLUMOSCIENCE INC., Montreal (CA)

( * ) Notice: Subject to any disclaimer, the term of this patent is extended or adjusted under 35 U.S.C. 154(b) by 948 days.

This patent is subject to a terminal disclaimer.

(21) Appl. No.: 13/067,914

(22) Filed: Jul. 7, 2011

(65) Prior Publication Data

US 2012/0082619 A1    Apr. 5, 2012

Related U.S. Application Data

(63) Continuation of application No. 12/149,989, filed on May 12, 2008, now Pat. No. 8,475,764, which is a continuation-in-part of application No. PCT/CA2005/000791, filed on May 24, 2005.

(60) Provisional application No. 60/573,334, filed on May 24, 2004.

(51) Int. Cl.
*A61K 51/00* (2006.01)
*A61M 36/14* (2006.01)
*C07K 14/575* (2006.01)
*A61K 51/08* (2006.01)

(52) U.S. Cl.
CPC ............ *C07K 14/575* (2013.01); *A61K 51/088* (2013.01)

(58) Field of Classification Search
CPC ....... A61K 47/00; A61K 47/30; A61K 47/42; A61K 47/48; A61K 49/00; A61K 49/0002; A61K 49/0056; A61K 49/14; A61K 51/00; A61K 51/06; A61K 51/08; A61K 51/088; A61K 38/00; A61K 38/16; A61K 38/17; A61K 2123/00; A61K 2121/00; C07K 14/00; C07K 14/435; C07K 14/575; C07K 14/57527
USPC .......... 424/1.11, 1.65, 1.69, 9.1, 9.2, 9.3, 9.4, 424/9.5, 9.6; 514/1, 1.1, 21.3, 77.3, 773; 534/7, 10–16; 530/300, 307, 324
See application file for complete search history.

(56) References Cited

U.S. PATENT DOCUMENTS

| | | | |
|---|---|---|---|
| 5,443,816 A | 8/1995 | Zamora et al. | |
| 6,268,474 B1 | 7/2001 | Smith et al. | |
| 6,440,421 B1 | 8/2002 | Cornish et al. | |
| 8,475,764 B2 * | 7/2013 | Dupuis et al. | 424/1.69 |
| 8,703,098 B2 * | 4/2014 | Dupuis et al. | 424/1.65 |

FOREIGN PATENT DOCUMENTS

| | | |
|---|---|---|
| CA | 2567478 | 5/2005 |
| WO | 9522341 A1 | 8/1995 |
| WO | 9640289 A1 | 12/1996 |
| WO | 9640293 A1 | 12/1996 |
| WO | 9802192 A1 | 1/1998 |
| WO | 9849196 A1 | 11/1998 |
| WO | 2004032708 A1 | 4/2004 |
| WO | WO 2004/032708 A2 | 4/2004 |
| WO | WO 2004/045592 A2 | 6/2004 |
| WO | 2005116065 A1 | 12/2005 |
| WO | 2006094725 A1 | 9/2006 |

OTHER PUBLICATIONS

Hinson, Joy Patricia et al. Adrenomedullin, a Multifunctional Regulatory Peptide. Endocrine Society vol. 21 No. 2 138-167 Sep. 2006 USA.
Naoteru Hirayama et al. Secretion and Clearance of the Mature Form . . . Elsevier Science Inc. vol. 64 No. 26 2505-2509 Mar. 1999 Japon.
T. Nishikimi et al Clinical Studies on the Sites of Production and Clearance . . . American Heart Ass. 1994;24 600-604 1994. USA.
Toshio Nishikimi et al Production and Clearance Sites of Two Molecular Forms of Adrenomedullin in Human Plasma Elsevier Science Inc. vol. 13 No. 9 1032-1034 Sep. 2000 USA.
Toshio Nishikimi et al The Active Molecular Form of Plasma Adrenomedullin Is Extracted in the Pulmonary . . . The Biochemical Society. Clinical Science (2001) 61-66 Sep. 2000 JP.
Ichiki, Y. et al., "Distribution and characterization of immunoreactive adrenomedullin in human tissue and plasma", FEBS Letters (Jan. 1994), vol. 338, pp. 6-10.
Kakishita at al., "Increased Plasma Levels of Adrenomedullin in Patients With Pulmonary Hypertension", Clinical Science (Jan. 1999), vol. 96, pp. 33-39.
Hasegawa et al., Autoradiographic Studies on the Binding Sites of 125I-Adrenomedullin in Rat Tissues, ACTA Histoghem Gytoghem, (Jan. 1998), vol. 31, No. 4, pp. 335-343.
Bolton, A.E. et al.,"The labelling of proteins to high specific radioactivities by conjugation to a 125I-containing acylating agent. Application to the radioimmunoassay" Biochem. J. (Feb. 1973) 133 (pp. 529-538).
Satoru et al. (1994) Structure-Activity Relationship of Adrenomedullin, a Novel Vasodilatory Peptide . . . The Endocrine Society. Jul. 26, 1994, pp. 2454-2458, vol. 135 No. 6 USA.

(Continued)

*Primary Examiner* — D L Jones

(57) ABSTRACT

The present invention relates to an adrenomedullin derivative including an adrenomedullin peptide, or a fragment thereof chelated or otherwise bound to at least one active agent. Examples of active agents include a paramagnetic element, a radioactive element and a fibrinolytic agent, among others. Paramagnetic agents have a distribution that is relatively easily shown through Magnetic Resonance Imaging (MRI). Radioactive agents have applications in imaging and delivery of radiations, depending on the specific element included in the active agent. Delivery of fibrinolytic agents mainly to a specific organ, such as for example to the lungs, allows to substantially improve the specificity and efficacy of thrombolytic therapy by allowing local delivery of the fibrinolytic agent, thereby reducing the risks of major bleeding in the therapy of the organ. If the organ is the lungs, a non-limiting example of pathology treatable with the fibrinolytic agent is pulmonary embolus.

2 Claims, 32 Drawing Sheets

(56) References Cited

OTHER PUBLICATIONS

Kitamura, K. et al. (1994) Cloning and Characterization of CDNA Encoding a Precursor for Human Adrenomedullin. Biochem. Biophys. Res. Commun. 194, 720-725 Jun. 1993.
Sugo, S., Minamino, N., Kangawa, K. et al. (1994) Endothelial Cells Actively Synthesize and Secrete Adrenomedullin. Biochem. Biophys. Res. Commun. 201, 1160-1166 Jun. 1994.
Hinson, J. P., Kapas, S. and Smith, D. M. (2000) Adrenomedullin, A Multifunctional Regulatory Peptide.Endocr. Rev. 21, 138-167 Apr. 2000.
Hay, D. L. and Smith, D. M. (2001) Receptors: Molecular Identity and Function. Peptides 22, 1753-1763 Jun. 2001.
Kuwasako, K., Kitamura, K., Ito, K. et al. (2001) The Seven Amino Acids of Human RAMP2 . J. Biol. Chem. 276, 49459-49465 Oct. 2001.
Poyner, D. R., Sexton, P. M., Marshall, I. et al. (2002) International Union of Pharmacology. XXXII. The Mammalian. Pharacol. Jun. 2002 rev. 54, 233-246.
Eguchi, S., Hirata, Y., Iwasaki, H. et al. (1994) Structure-Activity Relationship of Adrenomedullin, A Novel Vasodilatory Peptide. Endocrinolog 135, 2454-2458 Jul. 1994.
Sabates, B., Granger, T., Choe, E. et al. (1996) Adrenomedullin is Inactivated in the Lungs of Neonatal Piglets. J. Pharm. Pharmacol. 48, 578-580 Jan. 1996.
Hirayama, N., et al. (1999) Secretion and Clearance of the Mature Form of Adrenomedullin in Humans. Life Sci. 64, 2505-2509 Mar. 1999.
Nishikimi, T., Kitamura, K., Saito, Y. et al. (1994) Clinical Studies on the Sites of Production and Clearance of Circulating. Hypertension 24, 600-604 Jul. 1994.
Nishikimi, T., Matsuoka, H., Shimada, K., Matsuo, H. and Kangawa, K. (2004) Production and Clearance Sites . Plasma.Am. J. Hypertens. 13, 1032-1034 Sep. 2000.
Nishikimi, T. et al. (2001) The Active Molecular Form of Plasma Adrenomedullin is Extracted. Clin. Sci. 100, 61-66 Sep. 2000.
Dupuis, J., Goresky, C. A. and Fournier, A. (1996) Pulmonary Clearance of Circulating Endothelin-1 in Dogs In Vivo. J. Appl. Physiol. 81, 1510-1515 May 1996.
Kitamura, K., Kato, J., Kawamoto, M. et al. (1998) The Intermediate Form of Glycine-Extended Adrenomedullin. Biochem. Biophys. Res. Commun. 244, 551-555 Feb. 1998.
Martinez, A., Miller, M. J., Gatt, K. J. and Cuttitta, F. (1997) Adrenomedullin Receptor Expression in Human Lung and in Pulmonary. J. Histochem. Cytochem. 45,159-164 Oct. 1996.
Owji, A. A., Smith, D. M., Coppock, H. A. et al. (1995) An Abundant and Specific Binding Site for the Novel Vasodilator Adrenomedullin. Endocrinology 136,May 1995 2127-2134.
Poyner, D. R. (1997) Molecular Pharmacology of Receptors for Calcitonin-Generelated Peptide, Amylin and Adrenomedullin. Biochem. Soc. Trans. 25, 1032-1036 Mar. 1997.
Dschietzig, T., Azad, H. A., Asswad, L.. Somme. C., Bartsch. C. and Baumann, G. (2002) The Adrenomedullin Receptor Acts . Biochem. Biophys. Res. Commun. 294, 315-318 Apr. 2002.
Oing, X. Svaren. J. et al (2001) MRNA Expression of Novel CGRP1 Receptors and Their Activity-. Am. J. Physiol. Lung Cell. Mol. Physiol. 280, L547-L554 Oct. 2000.
Nagae, T., Mukoyama, M., Sugawara, A. et al. (2000) Rat Receptor-Activity-Modifying Proteins (RAMPS). Biochem. Biophys. Res. Commun. 270, 89-93 Feb. 2000.
Hagner, S., Haberberger, R., Hay, D. L. et al. (2003) Immunohistochemical Detection of the Calcitonin Receptor-Like Receptor. Eur. J. Pharmacol. 481, 147-151 Sep. 2003.
Hagner, S., Stahl, U., Knoblauch, B., McGregor, G. P. and Lang, R. E. (2002) Calcitonin Receptor-Like Receptor. Cell Tissue Res. 310,41-50 Aug. 2002.
Dilworth, J. R. and S. J. Parrott (1998). "The Biomedical Chemistry of Technetium and Rhenium." Chem. Soc. Rev. 27: 43-55. Aug. 1997.
Dupuis, J., A. Caron, et al. (2005). "Biodistribution, Plasma Kinetics and Quantification of Single Pass Pulmonary Clearance of Adrenomedullin." Clin Sci 1: Mar. 1, 2005.

Hom, R. K. and J. A. Katzenellenbogen (1997). "Technetium-99M-Labelled Receptor-Specific Small-Molecule." Nucl Med Biol 24(6): 485-98. Apr. 1997.
Kitamura, K., J. Sakata, et al. (1993). "Cloning and Characterization of CDNA." Biochem Biophys Res Commun 194(2): 720-5. Jun. 1993.
Liu, S. and D. S. Edwards (1999). "99MTC-Labelled Small Peptides as Diagnostic Radiopharmaceuticals." Chem Rev 99(9): 2235-68. May 1999.
Forest. M. & Fournier. A.: BOP Reagent for the Coupling of PGLU and BOC HIS (TOS) in Solid Phase. Inter. Journal of Peptide and Protein Research, 1990; 35: 89-94 Jul. 1989.
McLaughlin VV, McGoon MD. Pulmonary Arterial Hypertension. Circulation 2006;114:1417-1431. Sep. 2006.
Reindel JF, Ganey PE, Wagner JG, Slocombe RF, Roth RA. Development of Morphologic, Hemodynamic, and Biochemical. Toxicol Appl Pharmacol 1990;106:179-200 Aug. 1990.
Zhao YD, Courtman OW, Deng Y, Kugathasan L, Zhang Q, Stewart DJ. Rescue of Monocrotaline-Induced Pulmonary Arterial Hypertension. Circ Res 2005;96:442-450 Feb. 2005.
Gibbons C, Dackor R, Dunworth W, Fritz-Six K, Caron KM. Receptor Activity-Modifying Proteins: Ramping Up Adrenomedullin Signaling. Mol Endocrinol 2007;21:783-796 Oct. 2006.
Su AI, Cooke MP, Ching KA, Hakak Y et al. Large-Scale Analysis of the Human and Mouse Transcriptomes, Proc Nail Acad Sci U S A 2002;99:4465-4470 Jan. 2002.
Ono Y, Okano I, Kojima M, Okada K, Kangawa K. Decreased Gene Expression of Adrenomedullin Receptor in Mouse . Biochem Biophys Res Commun 2000;271:197-202 Mar. 2000.
Kurozumi T, Tanaka K, Kido M, Shoyama Y. Monocrotaline-Induced Renal Lesions. Exp Mol Pathol 1983;39:377-386 Jul. 1983.
Yoshihara F et al. Upregulation of Intracardiac Adrenomedullin and Its Receptor System in Rats Hypertrophy. Regul Pept 2005;127:239-244 Jan. 2005.
Wang X, Nishikimi T, Akimoto K, Tadokoro K, Mori Y, Minamino N. Upregulation of Ligand, Receptor System, N. J Hypertens 2003;21:1171-1181 Feb. 2003.
Lewis et al (Clinical Chemistry, 1996, vol. 44, No. 3, pp. 571-577).
Hinson et al (Endocrine Reviews, 2000, vol. 1, No. 2, pp. 138-167).
Office action issued by the European Patent Office on Feb. 2, 2009 for European Patent Application 05748704.3, corresponding to PCT application PCT/CA2005/000791 from which the present application claims priority.
Office action issued by the Canadian Intellectual Property Office on Feb. 10, 2012 for Canadian Patent Application 2,567,478, corresponding to PCT application PCT/CA2005/000791 from which the present application claims priority.
Office action issued by the Canadian Intellectual Property Office on Jan. 15, 2013 for Canadian Patent Application 2,567,478, corresponding to PCT application PCT/CA2005/000791 from which the present application claims priority.
Office action issued by the Canadian Intellectual Property Office on Jul. 24, 2013 for Canadian Patent Application 2,686,760, corresponding to U.S. Appl. No. 12/149,989 from which the present application claims priority.
Dumont et al., "Receptor autoradiography as mean to explore the possible functional relevance of neuropeptides: focus on new agonists and antagonists to study natriuretic peptides, neuropeptide Y and calcitonin gene-related peptides.", Peptides. Mar. 2004;25(3):365-91.
Egushi et al., "Structure-activity relationship of adrenomedullin, a novel vasodilatory peptide, in cultured rat vascular smooth muscle cells."Endocrinology. Dec. 1994;135(6):2454-8.
Greenland et al., "Water-soluble phosphines for direct labeling of peptides with technetium and rhenium: insights from electrospray mass spectrometry."Bioconjug Chem. Jul.-Aug. 2005;16(4):939-48.
International Preliminary Report on Patentability and Written Opinion issued by the World Intellectual Property Organization on Nov. 29, 2006 for PCT application PCT/CA2005/000791 from which the present application claims priority.
US Patent 8,703,098 issued on Apr. 22, 2014—whole prosecution history thereof.

(56) References Cited

OTHER PUBLICATIONS

US Patent 8,475,764 issued on Jul. 2, 2013—whole prosecution history thereof.

International Preliminary Report on Patentability and Written Opinion issued by the World Intellectual Property Organization on Nov. 29, 2006 for PCT application PCT/CA2008/000934, corresponding to U.S. Appl. No. 12/149,989 from which the present application claims priority.

Juaneda, C et al., "Adrenomedullin receptor binding sites in rat brain and peripheral tissues" European Journal of Pharmacology Aug. 2003, vol. 474, Issues 2-3, pp. 165-174.

Office action issued by the European Patent Office on Oct. 20, 2009 for European Patent Application 05748704.3, corresponding to PCT application PCT/CA2005/000791 from which the present application claims priority.

Office action issued by the European Patent Office on Apr. 12, 2011 for European Patent Application 08757094.1, corresponding to U.S. Appl. No. 12/149,989 from which the present application claims priority.

Office action issued by the European Patent Office on Sep. 10, 2010 for European Patent Application 05748704.3, corresponding to PCT application PCT/CA2005/000791 from which the present application claims priority.

Supplementary search report issued by the European Patent Office on Oct. 1, 2008 for European Patent Application 05748704.3, corresponding to PCT application PCT/CA2005/000791 from which the present application claims priority.

Supplementary search report issued by the European Patent Office on Jun. 25, 2010 for European Patent Application 08757094.1, corresponding to U.S. Appl. No. 12/149,989 from which the present application claims priority.

* cited by examiner

Pulmonary kinetics of $^{125}$I-rAM1-50 in dogs
A) Control
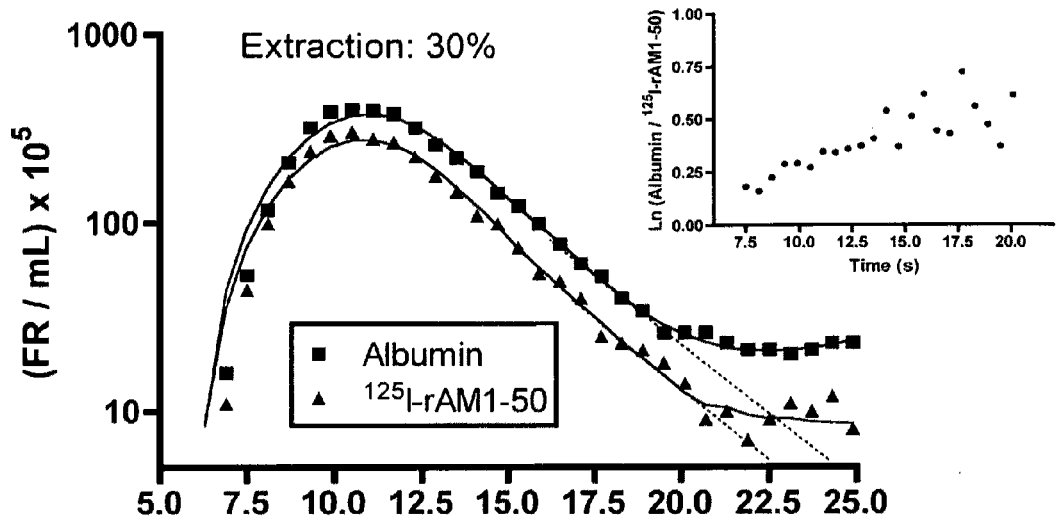
B) After injection of cold rAM1-50
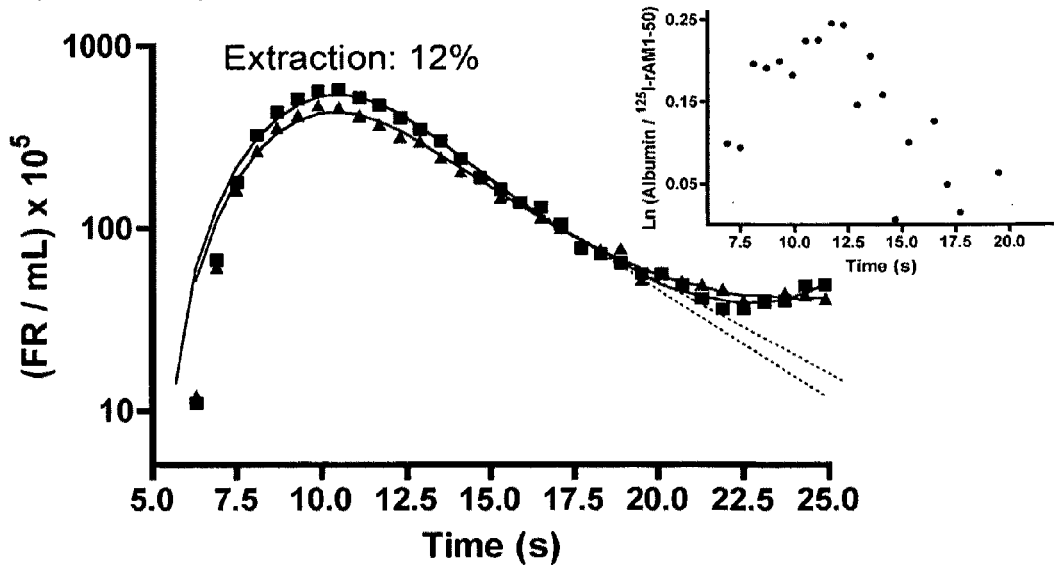
Figure 4

$T_{1/2}$ distribution (min) : 0.54
$T_{1/2}$ elimination (min) : 5.99

Gamma camera biodistribution corrected to back ground

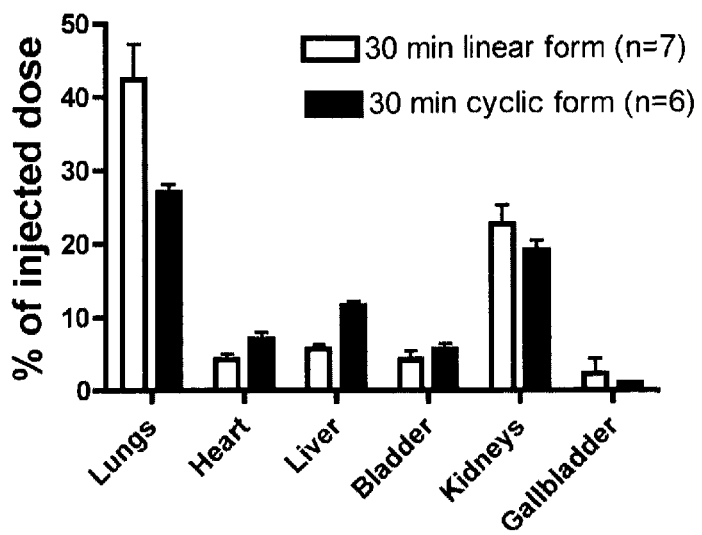
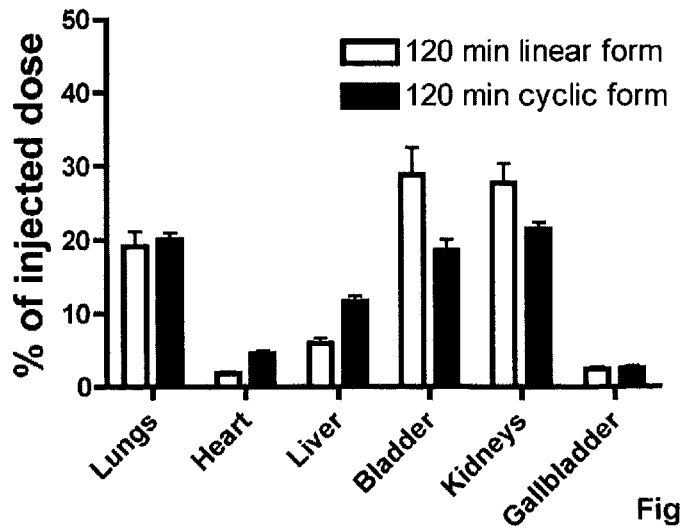
Figure 20

|  | hAM linear form | hAM cyclic form |
|---|---|---|
| $T_{1/2}$ distribution (min): | 1.67 | 1.75 |
| $T_{1/2}$ elimination (min): | 32.31 | 42.14 |

Structure-Activity of Adrenomedullin derivatives

| Derivative | Amino Acids Sequence and modifications | | | | | | | | | | | Cyclic (C) or Linear (L) | Lung Uptake | Hypotension At < 100 µg IV | Lung Dynamic plateau |
|---|---|---|---|---|---|---|---|---|---|---|---|---|---|---|---|
| | 1-12 | 13 | 14 | 15 | 16 | 17 | 18 | 19 | 20 | 21 | 22-52 | | | | |
| DTPA AM 1-52 | 1-12 | 13 | 14 | Gly | Cys | Arg | Phe | Gly | Thr | Cys | 22-52 | C | +++ | Yes | No |
| AM 13-52 | | | Ser | Phe | Gly | Cys | Arg | Phe | Gly | Thr | Cys | 22-52 | C | +++ | Yes | |
| AM 22-52 | | | | | | | | | | | 22-52 | L | No | No | |
| DFH-08 (6032Da) | 1-12 | Ser | Phe | Gly | Cys | Arg | Phe | Gly | Thr | Cys | 22-52 | L | +++ | Yes | No |
| DFH-09 (4249 Da) | | Ser | Phe | Gly | Cys | dPEG 2 | | | | Cys | 22-52 | L | ++ | Yes | No |
| DFH-10 (4337 Da) | | Ser | Phe | Gly | Cys | dPEG 4 | | | | Cys | 22-52 | L | ++ | No | No |
| DFH-11 (4083 Da) | | *GGaG* | | | | dPEG 4 | | | | | 22-52 | L | No | No | No |
| DFH-12 (4268Da) | | *GGaG* | | | Cys | dPEG 4 | | | | Cys | 22-52 | C | ++ | No | Yes |
| DFH-13 (4412 Da) | | *GGaG* | | | Cys-Acm | dPEG 4 | | | | Cys-Acm | 22-52 | L | No | No | No |
| DFH 14 (4204 Da) | | *GGG* | | | Cys | dPEG 4 | | | | Cys | 22-52 | L | ++ | No | |
| DFH 15 (4270 Da) | | *GGaG* | | | Cys | dPEG 4 | | | | Cys | 22-52 | L | ++ | No | |
| DFH 16 (4296 Da) | | *GGaG* | | | HomoCys | dPEG 4 | | | | HomoCys | 22-52 | C | ++ | No | |

The experiments were realized in dogs in vivo.

Figure 30

Rat Imaging comparison
DFH-08
DFH-12
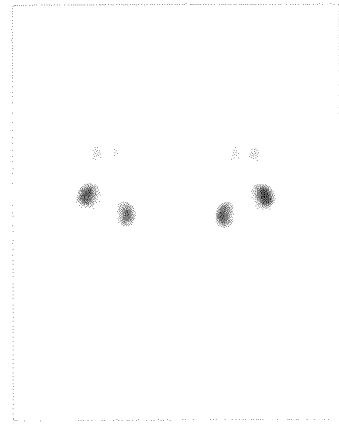
images at 30 min
Figure 33

LABELLED ADRENOMEDULLIN DERIVATIVES AND THEIR USE FOR IMAGING AND THERAPY

This application is a continuation of U.S. Utility patent application Ser. No. 12/149,989 filed May 12, 2008 now U.S. Pat. No. 8,475,764, which is a continuation-in-part of PCT Application PCT/CA2005/000791 filed May 24, 2005, which PCT application claimed priority from U.S. Provisional Patent Application Ser. No. 60/573,334 filed May 24, 2004 and which PCT application entered National Phase in the United States as U.S. Utility patent application Ser. No. 11/597,315 on Nov. 21, 2006.

FIELD OF THE INVENTION

The present invention relates to the use of labelled compounds for imaging or therapy. More specifically, the present invention is concerned with labelled adrenomedullin derivatives and their use for imaging and therapy.

BACKGROUND OF THE INVENTION

A currently existing agent for the clinical imaging of pulmonary circulation is $^{99m}$Tc-labelled albumin macroaggregates. This agent is used for the diagnosis of physical defects of the circulation due to pulmonary embolus. This agent is larger than small pulmonary vessels. Accordingly, further to being injected in an animal, this agent is trapped by these small pulmonary vessels, which enables external detection.

Important limitations of albumin macroaggregates include the inability to image the small pulmonary circulation beyond the point of obstruction. This limits the sensitivity of this substance to detect small vascular defects. Also, there are potential infectious risks since albumin macroaggregates are derived from human albumin. Additionally, albumin macroaggregates are unable to detect functional (biological) defects of the pulmonary circulation since their retention is uniquely dependent on physical characteristics of the vessels.

In addition, many other pulmonary diseases are difficult to diagnose. For example, pulmonary arterial hypertension (PAH) is a disorder characterized by endothelial dysfunction with intimal as well as vascular smooth muscle proliferation leading to gradual obliteration of pulmonary arterioles [36]. Screening for PAH is performed by transthoracic Doppler echocardiography with estimation of the pulmonary artery systolic pressure using the tricuspid valve regurgitant jet. Although this approach correlates with hemodynamically measured pulmonary pressure, it does not provide direct information on the biology of the pulmonary circulation and may miss the early presence of pulmonary vascular disease. The recent availability of oral therapies for PAH such as endothelin receptor antagonists and phophodiesterase inhibitors advocate for earlier diagnosis of this condition and treatment of subjects in functional class II. There is therefore imperious necessity for novel diagnostic approaches of this appalling condition that could provide earlier and more precise diagnosis.

There exist compounds that have an affinity for particular organs, such as for example adrenomedullin (AM). AM is a 52-amino-acid multifunctional regulatory peptide highly expressed in endothelial cells and widely distributed in various tissues [1,2]. The structure of AM is well conserved across species, with only six substitutions and two deletions in the rat [rAM(1-50)] compared with the human [hAM(1-52)] [3]. AM possesses structural homology with CGRP (calcitonin gene-related peptide), making it a member of the calcitonin/CGRP/amylin family (CT/CGRP/AMY peptide family).

The biological activities of AM are mediated by receptors composed of two essential structural components: a seven-transmembrane protein, the calcitonin receptor-like receptor (CRLR), and a single transmembrane domain termed RAMP (receptor-activity-modifying protein) [4,5]. The association of CRLR/RAMP1 represents the CGRP1 receptor and is not specific to AM. At the opposite, a specific AM receptor comes from the coupling of CRLR/RAMP2 or CLRL/RAMP3 [6]. This specific AM receptor can be blocked by the C-terminal AM fragment [hAM(22-52)] [7].

A biological action of AM is a potent hypotensive effect. The systemic hypotensive action of AM can however be reduced and sometimes abolished after intravenous compared with intra-arterial infusion [8], suggesting that the lungs have a potential to clear circulating AM and modulate its circulating levels. Many studies have confirmed that AM is cleared by the pulmonary circulation [9-12]. However, the relative contribution of the lungs to AM clearance in comparison with other organs has not been systematically evaluated and, more specifically, single-pass pulmonary clearance of AM has not been quantified in vivo. In addition, the exact region of the AM peptide that is responsible for the hypotensive effects is currently unknown.

Against this background, there exists a need in the industry to provide novel compounds having an affinity for the lungs, the kidneys and other organs, and more specifically to provide such compounds suitable for use in therapy and imaging.

The present description refers to a number of documents, the content of which is herein incorporated by reference in their entirety.

OBJECTS OF THE INVENTION

An object of the present invention is therefore to provide novel compounds having an affinity for the lungs.

SUMMARY OF THE INVENTION

In a first broad aspect, the invention provides an adrenomedullin derivative comprising: an adrenomedullin peptide or a fragment thereof bound with at least one active agent, the adrenomedullin peptide being a mammalian adrenomedullin peptide. In some embodiments, the active agent comprises a radioactive element. In other embodiments, the active agent includes any other suitable detectable label.

Typically, the adrenomedullin peptide comprises a peptide having the sequence: Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:1) or a fragment thereof and is in a linear form or in a cyclic form.

In some embodiments, the adrenomedullin peptide comprises an adrenomedullin fragment having the sequence: Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:2) or a fragment thereof In other embodiments, the adrenomedullin peptide comprises an adrenomedullin fragment having the sequence: X1-X2-X3-X4-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:3), wherein: X1 is absent or is selected from the group consisting of: Tyr-Arg-Gln-Ser-Met-Asn-Asn-Phe-Gln-Gly-Leu-Arg-Ser- Phe-Gly (SEQ ID NO:4), Ser-Phe-Gly (SEQ ID NO:5) and Gly-Gly-Ala-Gly (SEQ ID NO:6); X2 is Cys or HomoCys; X3 is Arg-Phe-Gly-Thr (SEQ ID NO:7) or a linear or branched PEG moiety having at least two Poly(ethylene glycol) (PEG) subunits; and X4 is Cys or HomoCys. In some examples, X3 is a linear PEG moiety having 2 or 4 PEG subunits. Advantageously, such PEG moieties have linear dimensions substantially similar to linear dimensions of an amino acid sequence that X3 replaces when compared to human AM. It is hypothesized that in these embodiments, the proposes AM has good biological properties as the structure of the AM is not modified greatly when compared to AM in which X3 is a peptide.

In a specific embodiment of the invention, X1 is Gly-Gly-dAla-Gly (SEQ ID NO:8). In other specific embodiments, X1 is Gly-Gly-Ala-Gly (SEQ ID NO:6), X2 is Cys, X3 is a linear moiety having 2 or 4 PEG subunits, and X4 is Cys.

In some examples, wherein the radioactive element is bound directly to an amino acid of the adrenomedullin peptide. Examples of radioactive element include: $^{99m}Tc$, $^{67}Ga$, $^{64}Cu$, $^{90}Y$, $^{161}Tb$, $^{177}Lu$, and $^{111}In$.

In some examples, the adrenomedullin peptide is in a linear form and the radioactive element is bound directly to a cysteine amino acid of the adrenomedullin peptide.

In other embodiments of the invention, the active agent comprises a paramagnetic element. In yet other embodiments of the invention, the active agent is an element selected from the group consisting of: Fe, Ca, Mn, Mg, Cu, and Zn. In yet other embodiments of the invention, the active agent is selected from the group consisting of: active agents comprising at least one paramagnetic element, active agents comprising at least one radioactive element, and fibrinolytic agents.

In another broad aspect, the invention provides a method of determining a disease state in an organ in a mammal, the organ comprising adrenomedullin-receptor-bearing cells, the method comprising: a) administering to the mammal a labelled adrenomedullin derivative in an effective amount to achieve binding between the labelled adrenomedullin derivative and the adrenomedullin-receptor-bearing cells; b) generating an image of the distribution of the labelled adrenomedullin derivative in the organ of the mammal; c) using the image of step b) to determine a labelling pattern of the adrenomedullin derivative in the organ; d) comparing the labelling pattern of step c) to a labelling pattern of a non diseased organ; and e) determining the disease state of the organ at least in part on the comparison of step d).

For example, the organ is a lung. In this example, in a specific example, the disease is pulmonary embolus and wherein the labelling pattern of step c) indicates that the labelled adrenomedullin derivative is present in a greater concentration in upstream regions of the lung than in downstream regions of the lung. Upstream and downstream regions are defined with respect to blood flow in the lungs. Detecting the pulmonary embolus may include identifying a labelling pattern in a region of the lung in which the labelled adrenomedullin derivative is present in a lower concentration than in adjacent regions of the lung. In another specific example, the disease is pulmonary arterial hypertension. And detecting the pulmonary arterial hypertension includes detecting a reduced uptake of the labelled adrenomedullin derivative as compared to a baseline uptake of the labelled adrenomedullin derivative in the non diseased organ, wherein the reduced uptake indicates pulmonary arterial hypertension.

In another example, the organ is a kidney and the disease is kidney damage. Determining the kidney damage may include identifying a labelling pattern in a region of the kidney in which the labelled adrenomedullin derivative is present in a lower concentration than in adjacent regions of the kidney. Determining the kidney damage may also include detecting a reduced uptake of the labelled adrenomedullin derivative as compared to a baseline uptake of the labelled adrenomedullin derivative in the non diseased organ, wherein the reduced uptake indicates kidney damage.

In some embodiments, the proposed method has one or more of the following features: the mammal is human; the labelled adrenomedullin derivative is administered to the mammal at a substantially hemodynamically inactive dose; the labelled adrenomedullin derivative is labelled with a radioactive element and the labelled adrenomedullin derivative is one of the labelled adrenomedullin derivatives described hereinabove.

In another broad aspect, the invention provides a method of determining the presence and density of adrenomedullin receptor-bearing cells in a mammal comprising: administering to the mammal an effective amount of labelled adrenomedullin derivative to achieve binding between the labelled adrenomedullin derivative and adrenomedullin-receptor-bearing cells; and determining the distribution of the labelled adrenomedullin derivative to obtain an image of the adrenomedullin-receptor-bearing cells.

In another broad aspect, the invention provides the use of labelled adrenomedullin derivatives to image the lungs or the kidneys of a mammal.

In another broad aspect, the invention provides, the invention provides an adrenomedullin derivative comprising: an adrenomedullin peptide, the adrenomedullin peptide comprising a peptide having the sequence: Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:1) or a fragment thereof, the adrenomedullin peptide being a mammalian adrenomedullin peptide. Examples of such adrenomedullin peptides are found hereinabove. In some embodiments the adrenomedullin derivative further comprises a chelating peptide covalently bound to the adrenomedullin peptide and at least one active agent bound to the chelating peptide.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 4 illustrates an example of indicator-dilution curve outflow profiles in the canine pulmonary circulation in control conditions (A) and after injection of unlabelled rAM(1-50) (B), Insets showing the natural log ratio curves of the tracers (FR is fractional recovery of each tracer);

FIG. 20, in a bar chart, illustrates the biodistribution in various organs of $^{99m}$Tc-cyclic AM and $^{99m}$Tc-linear AM 30 min and 60 min after intravenous injection in dogs;

FIG. 30 illustrates in table form various AM derivatives that were tested for biological activity;

FIG. 33 compares images obtained with two different adrenomedullin derivatives (identified by DFH-08 and DFH-12 in the table of FIG. 30) 30 minutes after injection in rats. Both tracers display detectable lungs and kidneys uptake. The DFH-12 however does not display as much liver activity enabling better delineation of the lungs.

DETAILED DESCRIPTION

Figure 1:
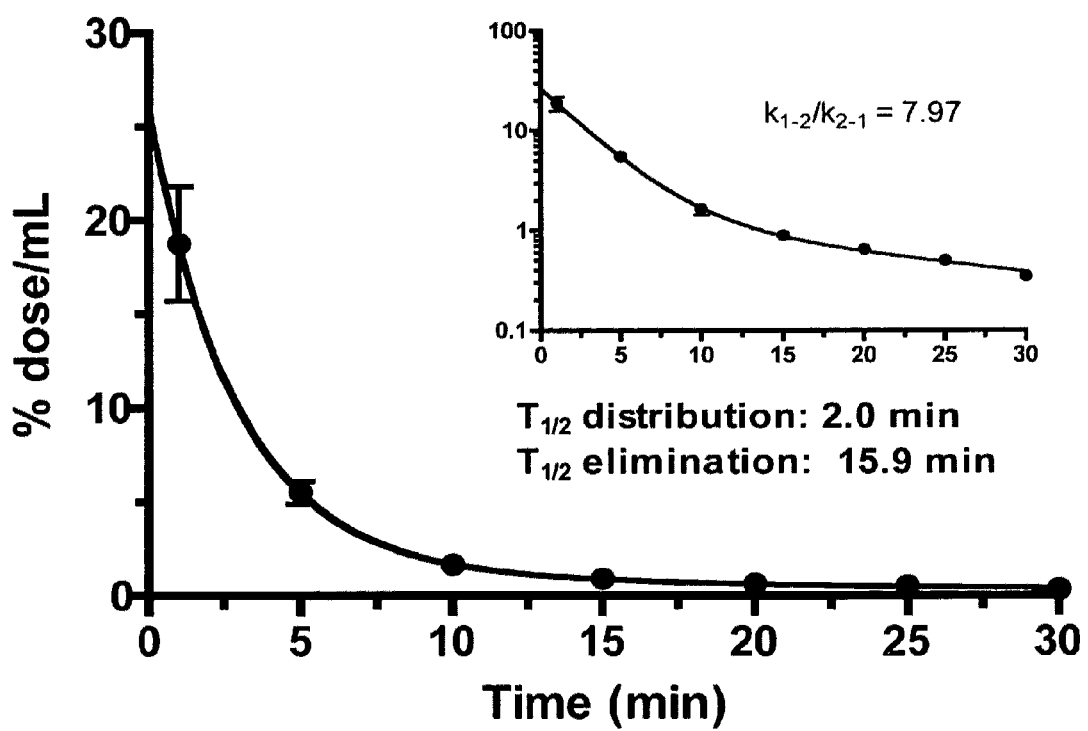
FIG. 1 illustrates the plasma kinetics of $^{125}I$-rAM(1-50) after a single intravenous injection in a rat.

The present invention relates to the use of an adrenomedullin derivative including an adrenomedullin peptide chelated to, or otherwise bound to, at least one active agent. For example, the adrenomedullin peptide comprises adrenomedullin having the sequence: Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-H is-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:1), or a fragment thereof. This adrenomedullin peptide corresponds to amino acids 1-52 of human adrenomedullin. Additionally, in other embodiments of the invention, fragments of adrenomedullin correspond to shorter peptide sequences, such as amino acids 1-50 of rat adrenomedullin or any other suitable fragment of any mammalian adrenomedullin.

Examples of active agents include a paramagnetic element, a radioactive element and a fibrinolytic agent, among others. Paramagnetic agents have a distribution that is relatively easily shown through Magnetic Resonance Imaging (MRI). Radioactive agents have applications in imaging and delivery of radiations, depending on the specific element included in the active agent. Delivery of fibrinolytic agents mainly to a specific organ, such as for example to the lungs, allows to substantially improve the specificity and efficacy of thrombolytic therapy by allowing local delivery of the fibrinolytic agent, thereby reducing the risks of major bleeding in the therapy of the organ. If the organ is the lungs, a non-limiting example of pathology treatable with the fibrinolytic is pulmonary embolus.

Non-limiting examples of radioactive elements suitable for imaging include: $^{99m}$Tc, $^{111}$In, $^{67}$Ga, $^{64}$Cu, $^{90}$Y, $^{161}$Tb, $^{177}$Lu, and $^{111}$In. Such agents may be complexed or otherwise bound, such bound directly to the adrenomedullin molecule or related derivative or chelated to the adrenomedullin related peptide through a chelator selected from: diethylenetriaminepentaacetic acid (DTPA), 1,4,7,10-tetraazacyclododecan-N, N',N'',N'''-tetraacetic acid (DOTA), 1,4,8,11-tetraazacyclotetradecane-N,N',N'',N'''-tetraacetic acid (TETA), and 6-hydrazinonicotinamide (HYNIC), among others.

EXAMPLE 1

A Process to Produce $^{99m}$Tc-Labelled AM.

In this example, the adrenomedullin produced is a human adrenomedullin having the sequence:

```
                                                          (SEQ ID NO.: 1)
H-Tyr-Arg-Gln-Ser-Met-Asn-Asn-Phe-Gln-Gly-Leu-Arg-Ser-Phe-Gly-Cys-

Arg-Phe-Gly-Thr-Cys-Thr-Val-Gln-Lys-Leu-Ala-His-Gln-Ile-Tyr-Gln-

Phe-Thr-Asp-Lys-Asp-Lys-Asp-Asn-Val-Ala-Pro-Arg-Ser-Lys-Ile-Ser-

Pro-Gln-Gly-Tyr-CONH₂
```

However, it is within the scope of the invention to use any other suitable adrenomedullin, such as rat adrenomedullin or derivatives of the CT/CGRP/AMY peptide family, as well as their modified products such as those obtained after N-terminal substitution, C-terminal substitution, or any other suitable substitution. In some embodiments of the invention, some of the amino acids are replaced by a non-amino acid moieties, as described in further details hereinbelow.

A method for synthesizing an a CT/CGRP/AMY peptide suitable for use with the present invention, such as for example adrenomedullin, was performed as follows. The following commercial N-α-fluorenylmethyloxycarbonyl [Fmoc]-L-amino acids were used: Alanine [Fmoc-Ala], Arginine-N$^{ω-}$(2,2,4,6,7-pentamethyldihydrobenzofuran-5-sulfonyl) [Fmoc-Arg(Pbf)], Asparagine-N$^{γ}$-trityl [Fmoc-Asn(Trt)], Aspartic acid-α-t-butyl ester [Fmoc-Asp(OtBu)], Cysteine-S-trityl [Fmoc-Cys(Trt)], Glutamine-N$^{δ}$-trityl [Fmoc-Gln(Trt)], Glycine [Fmoc-Gly], Histidine-N$^{im}$-trityl [Fmoc-His(Trt)], Isoleucine [Fmoc-Ile], Leucine [Fmoc-Leu], Lysine-N$^{ε}$-t-butyloxycarbonyl [Fmoc-Lys(Boc)], Methionine [Fmoc-Met], Phenylalanine [Fmoc-Phe], Proline [Fmoc-Pro], Serine-O-t-butyl [Fmoc-Ser(tBu)], Threonine-O-t-butyl [Fmoc-Thr(tBu)], Tyrosine-O-t-butyl [Fmoc-Tyr(tBu)] and Valine [Fmoc-Val].

Adrenomedullin and its CT/CGRP/AMY analogues were synthesized, using a solid phase procedure based on the Fmoc-amino acid chemistry—BOP reagent (benzotriazol-1-yl-oxy-tris(dimethylamino)-phosphonium hexafluorophosphate) coupling strategy. This procedure is better described in reference 35, which is hereby incorporated by reference.

In summary, a Fmoc-Rink-amide-acetamidonorleucylaminomethyl resin (4-(2',4'-dimethoxyphenyl-Fmoc-aminomethyl)-phenoxy-acetamidonorleucylaminomethyl resin) was used as the solid support. After a treatment with a 20% piperidine (Pip)-dimethylformamide (DMF) mixture, in order to remove the protecting Fmoc moiety and free the amine anchor on the solid support, the first amino acid of the synthesis, corresponding to the last residue of the peptide sequence (Tyrosine), was coupled to the resin with BOP reagent, in the presence of diisopropylethylamine (DIEA). In function of the resin substitution, a ratio of 3 equivalents (eq) of Fmoc-amino acid, 3 eq of BOP and 5 eq of DIEA was used for each coupling step and each step was monitored using a ninhydrin test.

After the complete synthesis of the peptide chain, a final Fmoc deprotection step was carried out with 20% Pip/DMF. For derivatives containing a N-terminal chelating functional, the resin-bound peptide was transferred into a round-bottom flask and the incorporation of a N-substituting moiety (examples of such moieties include, but are not limited to, diethylenetriaminepentaacetic acid (DTPA) or 1,4,7,10-tetraazacyclododecan-N,N',N'',N'''-tetraacetic acid (DOTA) or 1,4,8,11-tetraazacyclotetradecane-N,N',N'',N'''-tetraacetic acid (TETA or 6-hydrazinonicotinamide (HYNIC), among others) was achieved by mixing the resin-adrenomedullin overnight, at 50° C., with 3 eq of the substituting compound, 3 eq of BOP reagent and 3 eq of DIEA dissolved in a solvent mixture of DMF-dichloromethane-dimethylsulfoxide (49%:49%:2%).

The peptide was finally cleaved from the resin using a mixture of trifluoroacetic acid (TFA)-ethanedithiol (EDT)-phenol-H$_2$O (9.5 mL-0.25 mL-0.3 g-0.25 mL; 10 mL/g of resin) for 2 hours, at room temperature. After TFA evaporation, the crude material was precipitated and washed using diethylether. The peptide was then dried and kept at −20° C. until cyclization and purification.

AM cyclization, purification and characterization was performed, as follows. Crude adrenomedullin (AM) (200 mg) was dissolved in a 2 mL solution of 50% dimethylsulfoxide/H$_2$O in order to generate the disulfide bridge between the cysteine side-chains. After 30 min at room temperature, the peptide solution was diluted with 500 mL of 10% acetonitrile (ACN) in aqueous TFA (0.06%) before being injected onto a RP-HPLC C$_{18}$ (15 μm; 300 Å) column (250×21.20 mm) (Jupiter column from Phenomenex, Torrance, Calif.). The purification step was carried out using a Waters Prep 590 pump system connected to a Waters Model 441 absorbance detector. The flow rate was fixed at 20 mL/min and the peptide was eluted with a solvent gradient of 0% to 100% solvent B, in 2 h, where solvent A is 10% ACN in aqueous TFA (0.06%) and solvent B is 45% ACN in aqueous TFA (0.06%).

The homogeneity of the various fractions was evaluated using analytical RP-HPLC with a $C_{18}$ (5 µm; 300 Å) column (250×4.60 mm) ((Jupiter column from Phenomenex, Torrance, Calif.) connected to a Beckman 128 solvent module coupled to a Beckman 168 PDA detector. The flow rate was 1.0 mL/min and the elution of the peptide was carried out with a linear gradient of 20 to 60% B, where A is TFA 0.06% and B is ACN. Aliquots of 20 µl were injected and analyzed. Homogeneous fractions were pooled, lyophilized and then analyzed again by analytical HPLC, and by MALDI-TOF mass spectrometry (Voyager DE spectrometer—Applied Biosystems, Foster City, Calif.) using α-cyano-4-hydroxycinnamic acid as a matrix for peptide inclusion and ionization.

Labeling of a chelating adrenomedullin derivative (exemplified with DTPA-AM and $^{99m}$technetium) was as follows. The substituted peptide DTPA-AM (18.5 µg-2.89 nmol) was dissolved in 1 mM HCl (100 µl) and then, $SnCl_2.2 H_2O$ (14.8 µl of a 0.2 mg/mL aqueous solution: 3 µg-13 nmol) was added, followed immediately with $Na^{99m}TcO_4$ (15 mCi-28.9 pmol) in saline. After 1 h at room temperature, the solution was diluted with 1 mL of phosphate buffer-saline (PBS) at pH 7.4.

In other examples, adrenomedullin (AM) or AM fragments or AM analogues are modified with agents able to bind radioactive and/or paramagnetic chemical elements such as those from the following non limiting list: $^{99m}$technetium ($^{99m}$Tc), $^{111}$indium ($^{111}$In), $^{67}$gallium ($^{67}$Ga), $^{64}$copper ($^{64}$Cu), among others. In the present case, the modified AM, AM fragment or AM analogue is particularly suitable, but non-limitatively, for imaging with for instance, a gamma camera, a positron emission tomography camera, a magnetic resonance instrument, or any other suitable imaging device.

In other examples, adrenomedullin (AM) or AM fragments or AM analogues are modified with agents able to bind radioactive elements such as those from the following non exclusive list: $^{90}$yttrium ($^{90}$Y), $^{161}$terbium ($^{161}$Tb), $^{177}$lutetium ($^{177}$Lu), $^{111}$indium ($^{111}$In), among others. In this case, the modified AM, AM fragment or AM analogue are particularly suitable, but non-limitatively, for application in radiotherapy.

In other examples, adrenomedullin (AM) or AM fragments or AM analogues are modified with agents able to bind ions such as those produced from the elements appearing in the following non limiting list: iron (Fe), calcium (Ca), manganese (Mn), magnesium (Mg), copper (Cu), and zinc (Zn), among others. In the present case, the modified AM, AM fragment or AM analogues are particularly suitable, but non-limitatively, for application in chemotherapy, using, for example, an intracellular ion depletion strategy. In this particular case, possible chelating agents for ion depletion are selected from the following non-limiting list: desferioxamine, tachpyr (N,N',N''-tris(2-pyridylmethyl)-cis-1,3,5-triaminocyclohexane), among others.

While a specific process for producing a labeled adrenomedullin derivative according to the invention is described hereinabove, the reader skilled in the art will readily appreciate that it is within the scope of the invention to produce labeled adrenomedullin derivatives that are within the scope of the claimed invention in any other suitable manner.

EXAMPLE 2

Pharmacokinetics of $^{125}$I Labelled AM in Rats

Introduction

This example was designed to evaluate the biodistribution, pharmacokinetics and multiorgan clearance of AM in rats in vivo. Quantification of single-pass pulmonary kinetics of AM and its mechanism was characterized further in dogs using the single bolus indicator-dilution technique.

Methods

All experimental procedures were performed in accordance with the regulations and ethical guidelines from Canadian Council for the Care of Laboratory Animals, and received approval by the Animal Ethics and Research Committee of the Montreal Heart Institute. Male Sprague-Dawley rats (Charles River), weighing between 400-450 g, were anaesthetized by an initial intramuscular dose of xylazine (10 mg/kg of body weight) and ketamine (50 mg/kg of body weight), followed by an intra-peritoneal injection of heparin (2000 units; Sigma). Catheters were inserted into the right carotid artery and jugular vein. Heart rate and systemic blood pressure were monitored continuously. Additional doses of xylazine/ketamine were used if noxious stimuli (pinching the hind feet) elicited nociceptive motor reflexes or changes of the systemic blood pressure. Venous and arterial blood samples (3 ml) were collected and centrifuged (1875 g, 15 min, 4° C.) and the plasma saved for subsequent measurement of irAM (immunoreactive AM). A similar amount of saline was infused into the animals to prevent hypovolaemia.

Figure 2:
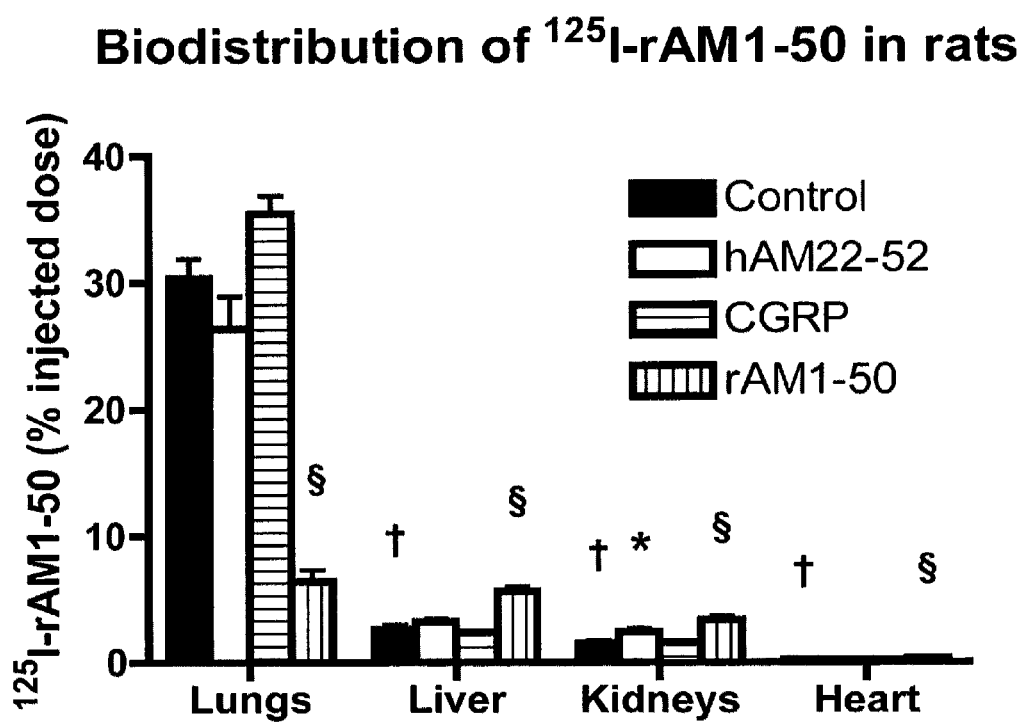
FIG. 2 illustrates the biodistribution of $^{125}I$-rAM(1-50) after intravenous injection in rats († $P<0.001$ compared with the lungs; * $P<0.005$ and §$P<0.001$ compared with control, n=10/group)

Radiolabelled $^{125}$I-rAM(1-50) (Amersham Biosciences) ($^{125}$I labelled rat adrenomedullin) was injected in a volume of 200 µl (0.3 pmol, 0.5 µCi) either into the right heart chambers via the right jugular vein catheter (n=10), or in the systemic circulation via the carotid catheter (n=10). A series of 200 µl blood samples were collected 1 min after the initial AM injection, then repeated every 5 min for a 30-min period. After each collection, an equal volume of saline was injected into the animal to maintain blood volume and pressure. The animals were then killed and the lungs, liver, kidneys (en bloc with the adrenal glands) and heart were removed and gravity drained. The blood samples and organs were then placed in a gamma-counter (model 1470 Wizard; Wallac) to determine $^{125}$I radioactivity. Results are expressed as a percentage of total radioactivity injected. Results for these experiments are shown in FIGS. 1 and 2.

Effects of Antagonists on AM Clearance

Figure 3:
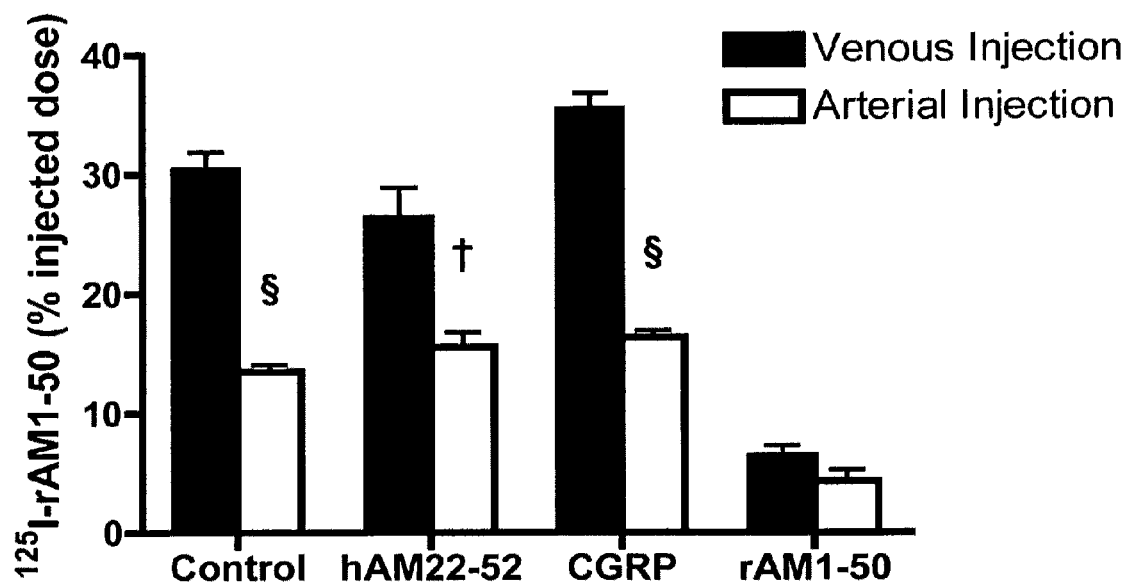
FIG. 3 illustrates the pulmonary retention of $^{125}I$-rAM(1-50) in rats after intravenous and intra-arterial injection († $P<0.005$ and §$P<0.001$ compared with venous injection, n=10/group)

Three groups of rats (n=20 in each) were studied and received either 200 µl of hAM(22-52) (5.6 nmol; Bachem), 100 µl of CGRP (1.75 nmol; Phoenix Pharmaceuticals) or 100 µl of unlabelled rAM(1-50) (17.5 nmol; American Peptide). The drugs were given by either intraarterial (n=10 in each group) or intravenous (n=10 in each group) injection 5 min before the $^{125}$I-rAM(1-50) bolus. Plasma samples and tissues were treated as described above. Results are shown in FIG. 3.

Measurement of Endogenous rAM(1-50) Levels in Plasma and Tissues

Plasma levels were measured in samples obtained at baseline as described above (n=40). In order to evaluate endogenous tissue levels, ten additional rats were studied. After being anaesthetized, the animals were killed by removal of the lungs, liver, kidneys and heart. Homogenization of organs was performed by adding 2 ml of buffer [4 mol/l guanidine thiocyanate (Fisher Scientific) and 1% trifluoroacetic acid (Sigma)] to 200 mg of tissue samples with the use of an automatic revolving pestle (DynaMix; Fisher Scientific). Homogenates were vortex-mixed and samples (100 µl) kept at 4 C for subsequent protein determination by Bradford analysis. Remaining samples were centrifuged at 1300 g (4 C) and the supernatant saved for processing. Tissues and plasma samples were extracted using Sep-Pak C18 cartridges (Waters) and irAM(1-50) was measured using a competitive RIA (Phoenix Pharmaceuticals) according to the manufacturer's instructions. The detection limit of this assay is approx. 4.7 pg/tube with a specificity for rAM(1-50) of 100%, without any cross reactivity (0%) with hAM(1-52), pro-hAM, pro-rAM, amylin and ET (endothelin)-1.

In Vivo Single-Pass Measurement of AM Clearance in Dogs

Dogs were anaesthetized and prepared as described in detail in reference [13], which is hereby incorporated by reference. A catheter was inserted into the carotid artery and positioned just above the aortic valve. This catheter was connected to a peristaltic pump for automated blood withdrawal. Another catheter was placed into the jugular vein and positioned in the right ventricular outflow tract to allow bolus injection of the study tracers. A bolus was prepared by adding 3.3 μCi of 125I-rAM(1-50) (2.9 pmol) to 3 ml of Evans-Blue-dye labelled albumin and 0.9% saline to give a final volume of 6 ml. The mixture was separated into three equal parts for the two successive experiments in each animal and to realize dilution-curve standards. A baseline single-bolus indicator-dilution experiment was performed. After 5 min, CGRP (n=7), hAM(22-52) (n=8) and unlabelled rAM(1-50) (n=9) were administered as an intravenous bolus of 100 nmol and 5 min later a second indicatordilution experiment was performed.

The collected samples were processed and indicator-dilution curves constructed and analyzed as described in previously cited reference 13. Cardiac output and mean tracer AM extraction during the pulmonary transit time were computed from the curves. Mean tracer extraction corresponded to the difference between the areas of the outflow curve of the vascular reference (albumin) and that of the extracted tracer (AM). Recirculation of the tracers apparent in the terminal portion of the curves was removed by linear extrapolation of the semi-logarithmic down slopes. Results are shown in FIG. 4.

Statistical Analysis

Multiple group comparisons were performed by factorial ANOVA, followed, when a significant interaction was found, by the Bonferroni/Dunn t test. Plasma kinetics of 125I-rAM (1-50) was fitted using a two-phase exponential decay equation with GraphPad Prism (version 4.0) software. Pulmonary clearance of 125I-AM(1-50) in rats after intravenous and intra-arterial injection was compared by two-tailed unpaired Student's t test. Comparison between venous and arterial rAM(1-50) levels in plasma was performed with a two-tailed paired Student's t test. In the canine experiments, the effect of drugs on AM extraction was analyzed by two-tailed paired Student's t tests. A P value of <0.05 was considered significant. All results are reported as means±S.E.M.

Results

Kinetics of $^{125}$I-rAM(1-50) in Plasma

As shown in FIG. 1, intravenously administered $^{125}$IrAM(1-50) rapidly decreased following a two-compartment model with a relatively rapid distribution half-life of 2.0 min [95% CI (confidence interval), 1.98-2.01] and an elimination half-life of 15.9 min (95% CI, 15.0-16.9). Compartmental analysis revealed that the ratio of rate constants for exchange between the central and peripheral compartments ($k_{1-2}/k_{2-1}$) was relatively high at 7.97, demonstrating an important distribution of drug into the peripheral compartment. The volumes of distribution were computed, including the volume of the central compartment (Vc=3.84 ml), the volume at steady state (Vss=12.5 ml) and the apparent volume of distribution (Varea=35 ml). Administration of a human AM fragment (hAM(22-52)), CGRP or unlabelled rAM(1-50) prior to the injection of radiolabelled rAM(1-50) did not modify plasma kinetics, resulting in almost perfectly superimposable curves (results not shown).

Biodistribution of 125I-rAM(1-50) After Injection

As shown in FIG. 2, the lungs predominantly retained the peptide 30 min after the injected dose (P<0.001). There was proportionately only minor retention by the liver, kidneys and heart. Administration of hAM(22-52) and CGRP did not significantly modify this distribution, except in kidneys, where only hAM(22-52) elevated the retained activity (P<0.005). Injection of unlabelled rAM(1-50) caused an important reduction in lung activity (P<0.001) and significantly increased (P<0.001) the amount retained by the liver, kidneys and heart.

Lung retention after intravenous compared with intra-arterial administration.

In the control group (n=10 per injection site), there was evidence of important first-pass pulmonary retention with a more than 50% decline in the amount of the peptide retained after intra-arterial compared with intravenous injection (FIG. 3). This pulmonary first-pass retention was not affected by prior administration of hAM(22-52) or CGRP. However, pre-treatment with rAM(1-50) did not decrease further the already lowered pulmonary retention after intra-arterial compared with intravenous injections.

Endogenous rAM(1-50) Levels in Plasma and Organs

There was no difference in I-rAM(1-50) levels in venous (3.1+−0.2 pmol/l) and arterial (3.2+−0.2 pmol/l) plasma (n=40). Tissue levels (n=10) were more than 20-fold higher in the lungs (249.0+−48.3 pg/mg protein; P<0.001) compared with liver (11.1+−1.3 pg/mg of protein), kidneys (11.7+−1.4 pg/mg of protein) and heart (7.2+−0.9 pg/mg of protein).

Single-Pass Pulmonary Kinetics of $^{125}$I-rAM(1-50) in Dogs In Vivo

Analysis of the indicator-dilution curve outflow profiles demonstrated a significant first-pass retention of $^{125}$I-rAM(1-50). A typical experiment is shown in the FIG. 4(A). The curve for $^{125}$I-rAM(1-50) progressively deviated from its vascular reference (labelled albumin). The recirculation of tracers was removed by extrapolation of the semi-logarithmic down slopes. The difference between the areas of the two tracers' curves, which represent mean tracer $^{125}$I-rAM(1-50) extraction during a single pulmonary transit time, was 30% in that experiment. Plotting the natural log ratio of the two tracers characterized further the extraction over time (FIG. 4). The relationship was found to be linear, demonstrating that extraction increased over time with no evidence of return of the extracted peptide into circulation. In terms of ordinary capillary modeling, the slope of this relationship represents the sequestration rate constant for $^{125}$I-rAM(1-50) by the lungs. In the same animal, a second experiment was performed after injection of unlabelled rAM(1-50) (FIG. 4B). There was an evident reduction in pulmonary clearance with a smaller differential curve area compared with albumin (mean extraction 12%) and progressively converging curves on the down slope. The log ratio is completely modified with an initial plateau followed by a decrease, demonstrating the return of the tracer into the circulation.

Mean single-pass pulmonary extraction of $^{125}$IrAM(1-50) was 36.4±2.1%. This was significantly decreased (P<0.01) to 21.9±2.4% after the administration of unlabelled rAM(1-50). Extraction was not affected by CGRP with 44.6±2.9% occurring in the control compared with 40.6±2.9% after administration. There was a slight but significant (P<0.01) decrease in extraction with hAM(22-52) from 40.0±1.7% before to 31.4±3.3% after administration.

Discussion

In this study, plasma kinetics and biodistribution of exogenously administered AM in rats as well as plasma and tissue levels of endogenous AM were evaluated. Single-pass pulmonary clearance of AM in dogs using the indicator-dilution technique was further quantified and characterized in vivo.

Injected AM has a relatively short elimination half-life of 16 min with rapid and important distribution into a peripheral compartment. The lungs retain most of the injected activity with evidence of single-pass clearance, since retention is lower after intra-arterial compared with intravenous injection. There was no difference in total endogenous I-rAM levels across the pulmonary circulation with very high endogenous tissue levels also found in the lungs compared with other organs. These data demonstrate that the lungs are a major site for AM clearance, the absence of a gradient suggesting that the lungs also have the ability to produce and release AM into the circulation.

A relatively small volume of distribution for the central compartment (3.5 ml) was found, which is, in fact, less than the total blood volume of the rat. This is consistent with the very rapid clearance of AM from plasma with evidence of a first-pass effect into the pulmonary circulation. Thus a substantial proportion of intravenously injected AM is relatively rapidly cleared as it passes through the pulmonary circulation and does not distribute into the systemic circulation. The importance of a first-pass pulmonary clearance was confirmed and quantified by the use of the indicator-dilution experiments in dogs where it was found that approximately 36% of the injected AM was retained within the few seconds of a single pulmonary transit time. The outflow profile demonstrates that the retained AM is bound to its clearance site and does not return into the circulation. This, combined with the data in rats, would suggest that AM binds with relatively high affinity and relatively irreversibly to its receptor. This is consistent with previous data demonstrating important specific AM binding sites in the lungs of rats and humans [15,16], with maximum binding in the lungs being higher than in any other organ studied [16]. This profile is reminiscent of the potent vasoconstrictor ET-1, which is also predominantly cleared by the pulmonary circulation by the endothelial ETB receptor [13].

The effects of AM are mediated by at least two different receptors [17]. One is the CGRP receptor to which AM binds with low affinity, whereas the other is considered a specific AM receptor that can blocked by the C-terminal fragment of AM, hAM(22-52). In the present study, it was found that $^{125}$I-rAM(1-50) clearance by the lungs can be competitively inhibited by the administration of unlabelled rAM(1-50). Interestingly, however, unlabelled rAM(1-50) did not modify the plasma kinetics of the peptide, as we observed a compensatory increase in retention by the liver, kidney and heart. This supports further the important clearance role of the lungs and suggests that most of the injected unlabelled AM was also retained by the lungs, explaining the lack of inhibition in peripheral organs where levels of $^{125}$I-rAM(1-50) must have been higher than those of the unlabelled peptide. There was no effect of similar doses of CGRP, demonstrating that the CGRP receptor is not responsible for pulmonary clearance. Administration of the C-terminal fragment hAM(22-52) also did not modify pulmonary retention in rats, although it did cause a small significant increase in the kidneys. These results were confirmed by the in vivo indicator-dilution studies in dogs where we found important first-pass extraction of $^{125}$I-rAM(1-50) which was importantly reduced after injection of unlabelled rAM(1-50), slightly reduced after hAM(22-52) and unaffected by CGRP. Previous investigators have evaluated pulmonary clearance of AM in isolated rat lungs and pulmonary endothelial cells and found that AM levels in effluents and culture media were unchanged after CGRP, but increased after administration of hAM(22-52) [18]. The structural components of the CGRP and AM receptors, CRLR, RAMP1, RAMP2 and RAMP3 are all expressed in rat lungs [19]. Northern-blot analysis has revealed previously that RAMP2, which confers AM selectivity to the receptor, is highly expressed in rat lung tissues compared with RAMP1 and RAMP3 [20]. Using selective CRLR antibodies and immunohistochemistry, Hagner et al. [21,22] demonstrated intense staining in the alveolar capillaries of both humans and rats. These previous findings, together with the present study, suggest that lung AM clearance is mediated by specific AM receptors, possibly at the level of the pulmonary vascular endothelium.

Conclusions

The lung is a primary site for AM clearance. There is important first-pass pulmonary clearance of AM through specific receptors. This suggests that the lungs not only modulate circulating levels of this peptide, but also represent its primary target.

EXAMPLE 3

Pharmacokinetics of 99mTc Labelled AM and Imaging Using Same

Widely accessible in most nuclear medical centres via $^{99}$Mo/$^{99m}$Tc generator. Technetium-99m shows suitable nuclear properties for nuclear imaging with γ-emitting of 140.5 keV and a short half-life of 6.01 h (34). To avoid strong perturbation of hAM1-52 chemical structure and, consequently, the loss of its biological properties during radiolabelling with $^{99m}$Tc, a successful procedure, called 'bifunctional approach', has been proposed. This strategy consists of tethering a strong chelating group for the radionuclide to a point of the peptide that is irrelevant for preserving its biological properties [23, 26, 31]. Thus, we developed chelated radiolabelled adrenomedullin derivatives, preferably a chelated hAM1-52 derivative using diethylenetriaminepentaacetic acid (DTPA) radiolabelled with $^{99m}$Tc.

The present example was designed to systematically evaluate the biodistribution, pharmacokinetics and multi-organic clearance of $^{99m}$Tc-DTPA-hAM1-52 in dogs in vivo. Furthermore, the purpose of this investigation was to assess the utility of the radiolabelled peptide as a pulmonary vascular imaging agent.

Anesthesia and Animal Preparation

All experimental procedures were performed in accordance with regulations and ethical guidelines from Canadian Council for the Care of Laboratory Animals, and received approval by the animal ethics and research committee of the Montreal Heart Institute. Mongrel dogs weighing between 20-30 kg and presenting negative Dirofilaria imitis blood test results were anesthetized by an initial intravenous dose of pentobarbital sodium (50 mg/kg). Animals were intubated and mechanically ventilated using room air. Cutaneous electrocardiographic leads were installed, and 18F cathlon with three-way was installed on both saphenous vein for 0.9% sodium chloride perfusion, radiolabelled injection and blood collection. A right arterial femoral catheter was also inserted using the Seldinger technique for continuous blood pressure monitoring. Additional doses of pentobarbital sodium were used if noxious stimuli (pinching near the eye) could elicit nociceptive motor reflexes or changes of the systemic blood pressure.

Dogs (n=10) undergoing surgical procedures were anesthetized and prepared as previously described, but maintained ventilated with 1-3% isoflurane. Pulmonary lobectomy was obtained by performing a surgical ligature of the right median lobe of the lungs.

Pharmacokinetics of 99mTc-DTPA-hAM1-52 in Plasma

Figure 5:
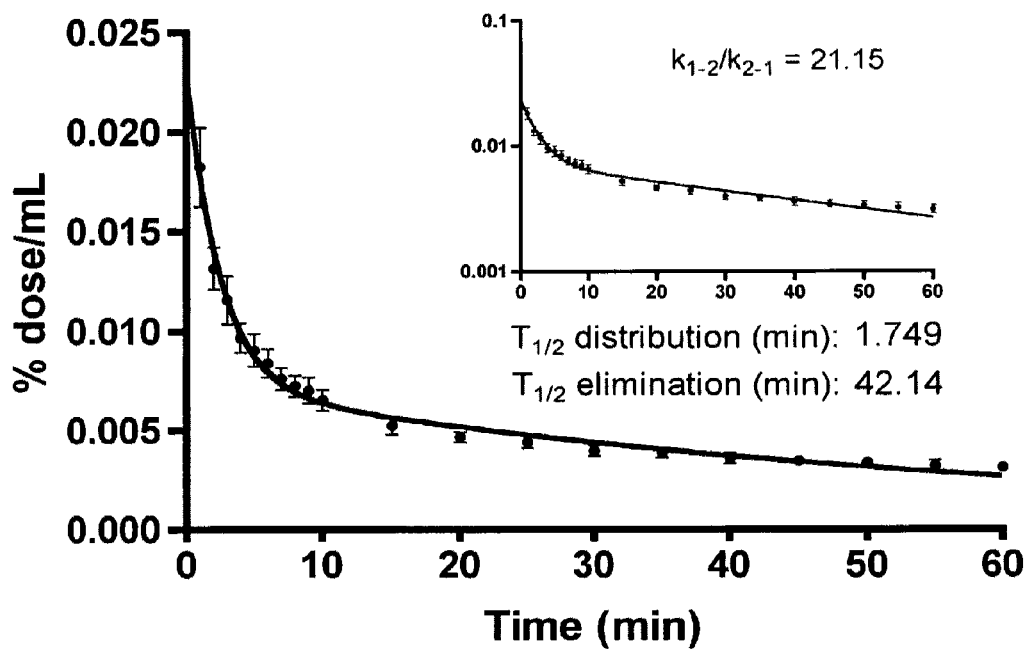
FIG. 5 illustrates the plasma kinetics of $^{99m}Tc$-DTPA-hAM1-52 after single intravenous injections in dogs, the data being fitted with a two-phase exponential decay equation (the inset shows a logarithmic scale, n=6/group)

Purified and buffered $^{99m}$Tc-DTPA-hAM1-52 samples were injected in right saphenous vein (n=6). A series of 2 mL blood samples were collected 1 min after the initial AM injection for a 10-min period, then repeated every 5 min for the following 50-min period. Blood samples were taken via left saphenous vein. After each collection, an equal volume of saline was injected into the animal to maintain blood volume and pressure. The blood samples were then placed in an automatic gamma counter (model 1272 Clinigamma, LKB Wallac, Finland) to determine $^{99m}$Tc activity. Results were expressed as a percentage of total radioactivity injected per mL and are shown in FIG. 5.

Biodistribution of 99mTc-DTPA-hAM1-52 and Multi-Organic Clearance In Vivo

Figure 6:
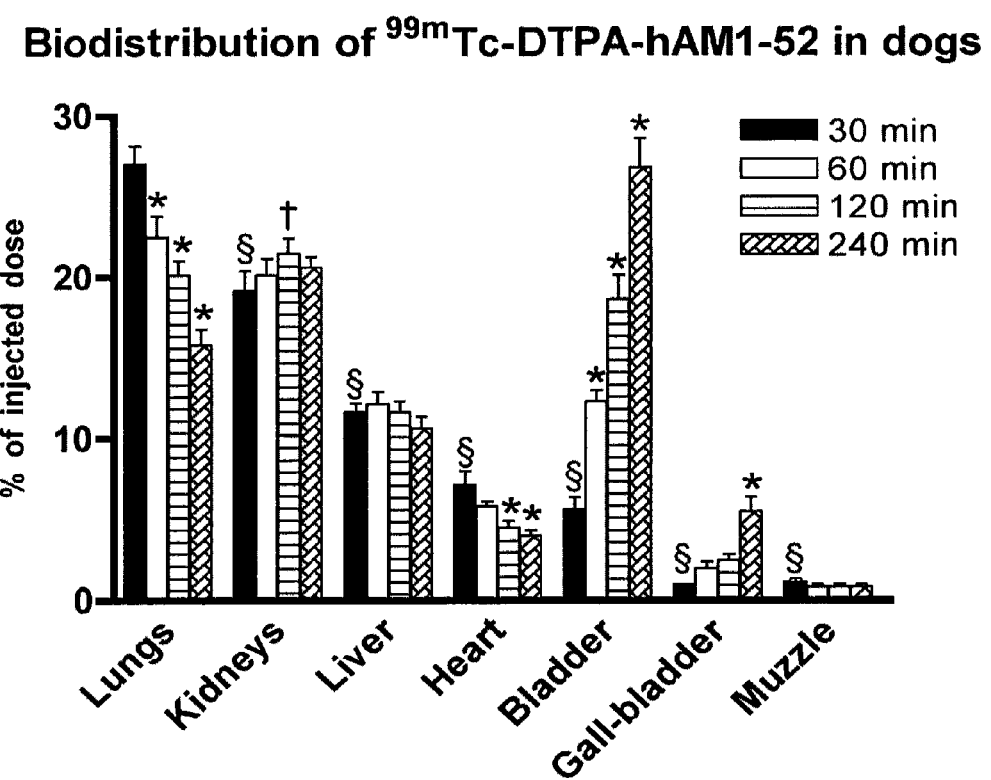
FIG. 6 illustrates the biodistribution of $^{99m}$Tc-DTPA-hAM1-52 after intravenous injection in dogs (†P<0.005 vs. 30 minutes; *P<0.001 vs. 30 minutes; §P<0.001 vs. lungs, n=6/group)
Figure 7:
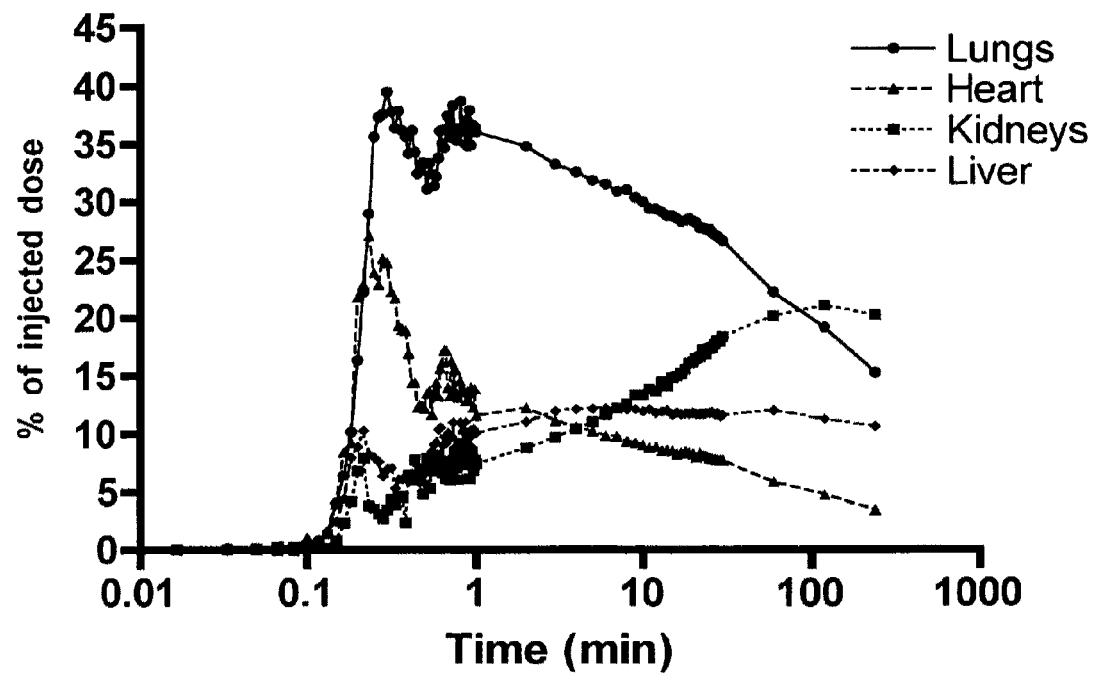
FIG. 7 illustrates the dynamic biodistribution of $^{99m}$Tc-DTPA-hAM1-52 after intravenous injection in dogs (n=6/group)

Multi-organic biodistribution of $^{99m}$Tc-DTPA-hAM1-52 was evaluated with an Anger camera (420/550 Mobile Radioisotope Gamma Camera; Technicare, Solon, Ohio, USA) equipped with on board computer, and a low-energy parallel-hole collimator (model 14S22014). Following intravenous injection of $^{99m}$Tc-DTPA-hAM1-52, dynamic acquisition of the lungs, heart, liver and kidneys was recorded for a 30-min period (one frame/sec during the first minute, then one frame/min for the remaining time). Static acquisitions was also recorded for whole individual organs, including lungs, kidneys, liver, heart, bladder, gallbladder and muzzle, at 30, 60, 120, 240 minutes after initial injection. These recordings were performed both in ventral and dorsal positions. Results are shown in FIGS. 6 and 7.

Gamma Camera Results Analysis

Figure 8:
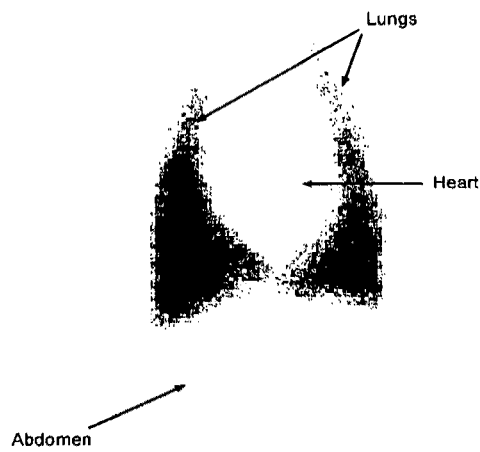
FIG. 8 is a gamma camera image of a dog's thorax obtained further to an injection of $^{99m}$Tc marked AM.
Figure 9:
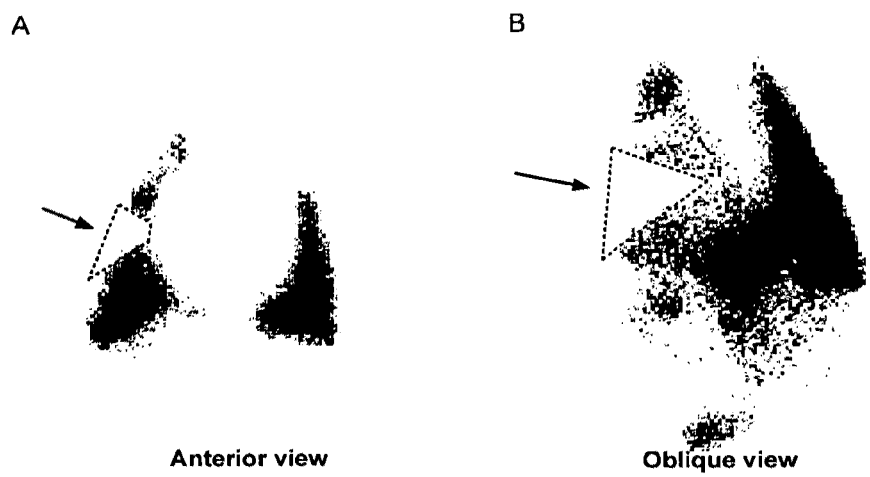
FIG. 9 illustrates selective surgical pulmonary lobectomy effects on $^{99m}$Tc-DTPA-hAM1-52 perfusion in dog as imaged through a gamma camera: (A) anterior view, (B) oblique view, a wedge shaped perfusion defect being indicated by an arrow and delimitated by dotted lines.

Dynamic and static acquisitions were evaluated by using Matlab version 7.01 image analysis tools software. The $^{99m}$Tc total count, $^{99m}$Tc mean count, and region of interest (ROI) size were calculated for each organ. Data correction was applied for 1) radioactive decay, 2) surgical table attenuation (dorsal images only), 3) geometric mean, and 4) organ's attenuation based on transmission factor. Results were expressed as a percentage of total radioactivity injected and examples of images obtained are shown in FIGS. 8 and 9.

Statistical Analysis

Plasma kinetics of $^{99m}$Tc-DTPA-hAM1-52 was fitted using a two-phase exponential decay equation with GraphPad Prism version 4.0 software. Time effects on each organ biodistribution were analyzed by two-way repeated measures ANOVA followed, when a significant interaction was found, by Bonferroni/Dunn t-test. Multiple organs biodistribution comparison at 30 minutes was performed by one-way ANOVA followed, when a significant interaction was found, by Bonferroni/Dunn t-test. A P values of <0.05 was considered significant. All results are reported as mean±S.D.

Results

Kinetics of $^{99m}$Tc-DTPA-hAM1-52 in Plasma (FIG. 5)

Intravenously administered $^{99m}$Tc-DTPA-hAM1-52 decreased relatively rapidly following a two-compartment model with a relatively rapid distribution half-life of 1.75 min (95% confidence interval, CI: 1.31-2.65) and an elimination half-life of 42.14 min (CI: 30.41-68.63). Compartmental analysis reveals that the ratio of rate constant for exchange between the central and peripheral compartments $(k_{1-2}/k_{2-1})$ is relatively high at 24.09, demonstrating an important distribution of drug into the peripheral compartment.

Biodistribution of $^{99m}$Tc-DTPA-hAM1-52 After Injection (FIG. 6)

The lungs predominantly retained the peptide with 27.00±2.76% of the injected dose after 30 minutes (P<0.001), as compared to kidneys (19.17±3.06%), liver (11.67±1.37%), heart (7.17±2.04%), bladder (5.67±1.75%), gallbladder (0.96±0.38%), and muzzle (1.17±0.41%). Lung retention was mildly reduced with time but sustained up to 4 hours after the injection (15.83±2.32%). Furthermore, uptake progressively increased in the bladder (26.83±4.36%) and gallbladder (0.83±0.41%), consequently to the excretion of the radiolabelled peptide. The $^{99m}$Tc-DTPA-hAM1-52 biodistribution in the kidneys, liver, and muzzle remained unchanged with time, with respectively 20.67±1.51%, 10.67±1.75%, and 0.83±0.41% at 240 minutes after peptide injection.

Dynamic Bioditribution $^{99m}$Tc-DTPA-hAM1-52 After Injection (FIG. 7)

Analysis of dynamic multi-organic biodistribution demonstrates significant pulmonary first pass retention of $^{99m}$Tc-DTPA-hAM1-52. The curve for lungs clearance also shows recirculation of the radiolabelled peptide, followed by a slow decrease with time. Moreover, heart curve indicates similar first pass retention of $^{99m}$Tc-DTPA-hAM1-52, without however sustained clearance with time. On the opposite, liver and kidneys dynamic biodistribution demonstrate only slow but continuous retention with time.

Selective Pulmonary Lobectomy Effects on $^{99m}$Tc-DTPA-hAM1-52 Perfusion (FIGS. 8 and 9)

Homogeneous distribution of the tracer is evident in the lungs of a normal animal (FIG. 8) with substantially no detectable activity over the region of the heart and little activity in the abdomen. This allows for good lung imaging without significant contaminant activity from surrounding organs. After surgical lobectomy mimicking the pathologic condition of a pulmonary embolus (FIG. 9), there is an evident perfusion defect which allows the diagnosis by external imaging. FIG. 9 shows images obtained through anterior (panel A) and oblique (panel B) views. The perfusion defect was substantially wedge-shaped. This defect is indicated by an arrow and substantially delimited by dotted lines.

EXAMPLE 4

Synthesis of Alternative Adrenomedullin Derivatives

Adrenomedullin and adrenomedullin fragments were synthesized as follows. These peptides were synthesized according to a procedure based on standard solid phase Fmoc peptide chemistry. Briefly, a Rink amide AM resin was used as the solid support and all couplings of N-α-Fmoc amino acids were performed in N,N-dimethylformamide (DMF) in the presence of benzotriazol-1-yl-oxy-tris(dimethylamino)-phosphonium hexafluorophosphate (BOP) and diisopropylethylamine (DIEA). Completion of the reaction was monitored using a ninhydrin test. Once the peptide chain was completed, cleavage from the resin was achieved with a 2 h treatment with a 95% trifluoroacetic acid (TFA) solution containing ethanedithiol, phenol, and water as scavengers. The solid support was then removed by filtration and, after TFA evaporation, the crude peptide was isolated by precipitation with diethylether. All chemicals used during the syntheses were from known suppliers.

The crude material was dissolved in water containing 0.06% TFA, at a concentration of 10 mg/ml. Dithiothreitol (5 eq) was added to ensure complete linearization of the peptide.

This solution was purified by means of reverse-phase HPLC using a C18 (5 µm, 110 Å, 250×21.2 mm) column and the peptide detection was carried out with a UV detector set at 229 nm. Elution was achieved over a 2 h linear gradient from A (water containing 0.06% TFA) to B (40% acetonitrile in A). The flow rate was maintained at 20 ml/min. Collected fractions were evaluated for their purity by analytical reverse-phase HPLC with a C18 (4 µm, 90 Å, 250×4.6 mm) column connected to a photodiode array detector. The flow rate was maintained at 1 ml/min and the elution was carried out with a 1 h linear gradient of 0% to 60% acetonitrile in aqueous 0.06% TFA. Homogeneous fractions were analyzed by MALDI-TOF mass spectrometry. Analyses were performed with a nitrogen laser (337 nm) and α-cyano-4-hydroxycinnamic acid was the matrix for ionization. Each mass spectrum was recorded in linear mode at an accelerating voltage of 25 kV. Fractions corresponding to pure linear AM were pooled, lyophilized and kept at −20° C. until further use.

A small amount of pure linear AM was dissolved in water at a concentration of 1 mg/ml and aliquots of 17.4 µl (2.89 nmol) were placed at the bottom of 2 ml sterile tubes. Aliquots were then frozen, lyophilized and kept at −20° C. until the $^{99m}$Tc labelling procedure, which was as follows.

Labeling of linear hAM(1-52) was realized using $^{99m}$Tc by a direct method. 100 ml of 1 mM hydrochloric acid was added to a reaction vial containing 18.5 mg of lyophilized linear hAM(1-52). Immediately thereafter, 14.8 mL of freshly prepared SnCl2 (0.2 mg/mL) solution was added. After addition of 0.2 ml of freshly eluted 99mTc-sodium pertechnetate (80-100 mCi/ml saline), the mixture was gently stirred and incubated for 1 h at room temperature.

In this and all the following examples, the adrenomedullin used is a human adrenomedullin, a fragment thereof, or a derivative of the human adrenomedullin having the sequence:

H-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-CONH$_2$(SEQ ID NO.: 1).

However, in alternative embodiments of the invention, the adrenomedullin is any other suitable mammalian adrenomedullin, such as rat, mouse, dog or other suitable mammalian adrenomedullin.

As compared to the experiments presented in examples 1 to 3, it has been found that linear adrenomedullin is able to directly bind to $^{99m}$Tc. It is hypothesized that $^{99m}$Tc binds to the molecule through coordination bonds involving the sulphur atoms of the free thiol functions of cysteines 16 and 21 of the above-described hAM. This type of bonding was described previously for salmon calcitonin, after reducing the disufide bridge (Bioconjugate Chem, 16, 939-948 [2005]). In addition, it is assumed that the nitrogen atoms of the peptide bond of both cysteines also participate the chelation process.

EXAMPLE 5

Bio-Distribution of $^{99m}$Tc-Linear AM

The bio-distribution of $^{99m}$Tc-linear AM, synthesized as described in Example 4, was studied in dogs as a function of time in various organs. $^{99m}$Tc-linear AM was injected in dogs and multi-organic biodistribution of $^{99m}$Tc-DTPA-hAM1-52 (synthesized as described hereinabove) was evaluated with an Anger camera (420/550 Mobile Radioisotope Gamma Camera; Technicare, Solon, Ohio, USA) equipped with on board computer, and a low-energy parallel-hole collimator (model 14S22014). Following intravenous injection of linear $^{99m}$Tc hAM1-52, dynamic acquisition of the lungs, heart, liver and kidneys was recorded for a 30-min period (one frame/sec during the first minute, then one frame/min for the remaining time). Static acquisitions were also recorded for whole individual organs, including lungs, kidneys, liver, heart, bladder, gallbladder and muzzle, at 30, 60, 120, 240 minutes after initial injection. These recordings were performed both in ventral and dorsal positions. Dynamic and static acquisitions were evaluated by using Matlab version 7.01 image analysis tools software. The $^{99m}$Tc total count, $^{99m}$Tc mean count, and region of interest (ROI) size were calculated for each organ. Data correction was applied for 1) radioactive decay, 2) table correction (dorsal images only), 3) geometric mean, and 4) organ's attenuation based on transmission factor. Results were expressed as a percentage of total radioactivity injected.

Figure 10:
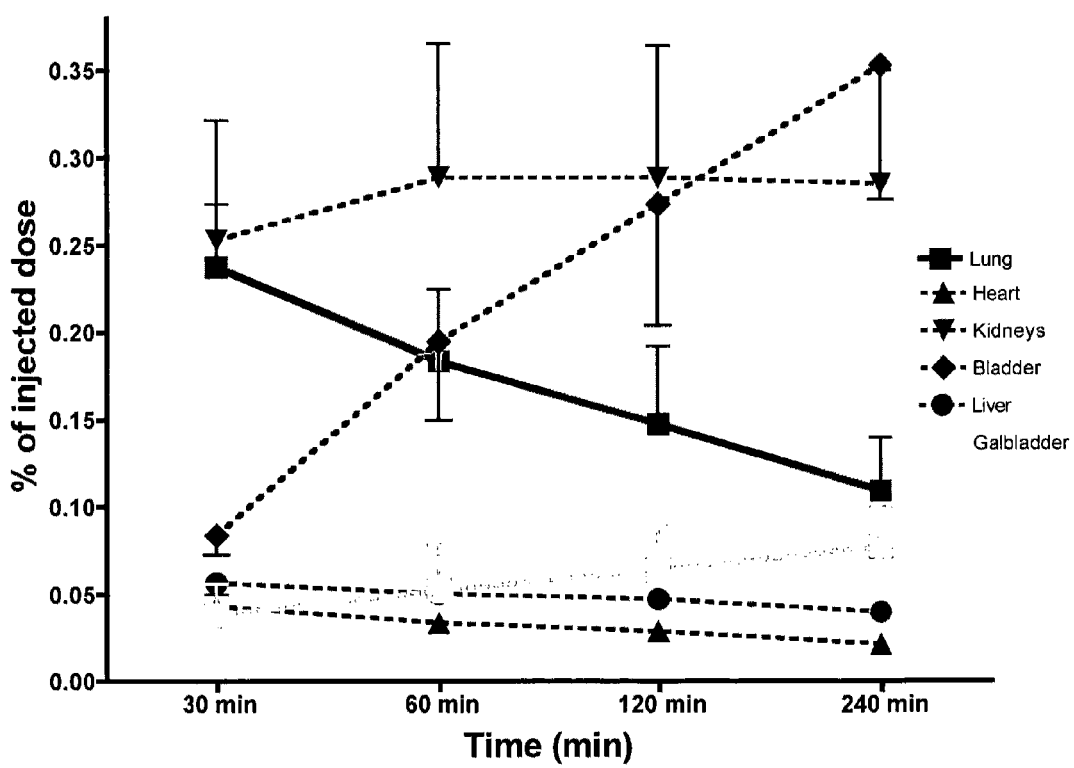
FIG. 10, in X-Y graphs, illustrates the time-dependent biodistribution in various organs of $^{99m}$Tc-linear AM after intravenous injection in dogs.

As seen from FIG. 10, $^{99m}$Tc-linear AM binds relatively selectively to the lungs with 24% retention and is only relatively slowly eliminated from this organ. These results are similar to results obtained using cyclic adrenomedullin presented in the previously referred to PCT application. Knowing that reduced linear AM is a weak ligand (Endocrinology, 135, 2454-2458 [1994]), these results suggest that the incorporation of $^{99m}$Tc between the sulfur atoms of the cysteine side-chains promotes the folding of the 16 to 21 segment of the molecule in a similar pattern to that found in native AM. Therefore, it can be postulated that labeled linear adrenomedullin and derivative thereof have a potential to be useful in the imaging of the lungs.

It should be noted that $^{125}$I, which is often use in preclinical biodistribution studies, is a radioactive element of practically no clinical value in human imaging due to its weak radioactive activity and potential thyroid toxicity. Therefore, the surprising result that some radioactive elements, such as $^{99m}$Tc, readily bind to linear AM indicates that linear AM is likely to be successfully used in lung imagery.

EXAMPLE 6

Plasma Kinetics of $^{99m}$Tc-Linear AM

The plasma kinetics of $^{99m}$Tc-linear AM was studied in 11 rats. $^{99m}$Tc-linear AM was injected in rats in a volume of 200 µl into the right jugular vein catheter. A series of 200 µl blood samples were collected 1 min after the initial injection, then repeated every 5 min for a 30-min period. After each collection, an equal volume of saline was injected into the animal to maintain blood volume and pressure. The animals were then sacrificed and the lungs, liver, kidneys (en bloc with the adrenal glands) and heart were removed and gravity drained. The blood samples and organs were then placed in a gamma counter (model 1470 Wizard, Wallac, Finland) to determine $^{99m}$Tc activity. Results were expressed as a percentage of total radioactivity injected.

Figure 11:
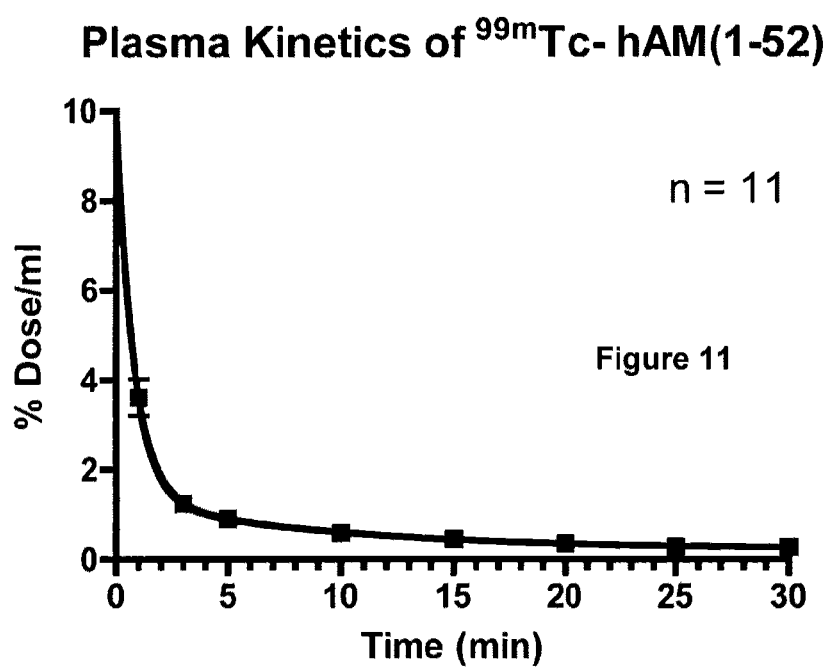
FIG. 11 in a X-Y graph, illustrates the plasma kinetics of $^{99m}$Tc-linear AM after a single intravenous injection in rats.

As seen from FIG. 11, $^{99m}$Tc-linear AM is cleared relatively rapidly from the plasma. The data illustrated in FIG. 11 was used to determine the parameters of two-compartment model, which gave a relatively rapid distribution half-life of 0.54 min and an elimination half-life of 5.88 min.

Figure 12:
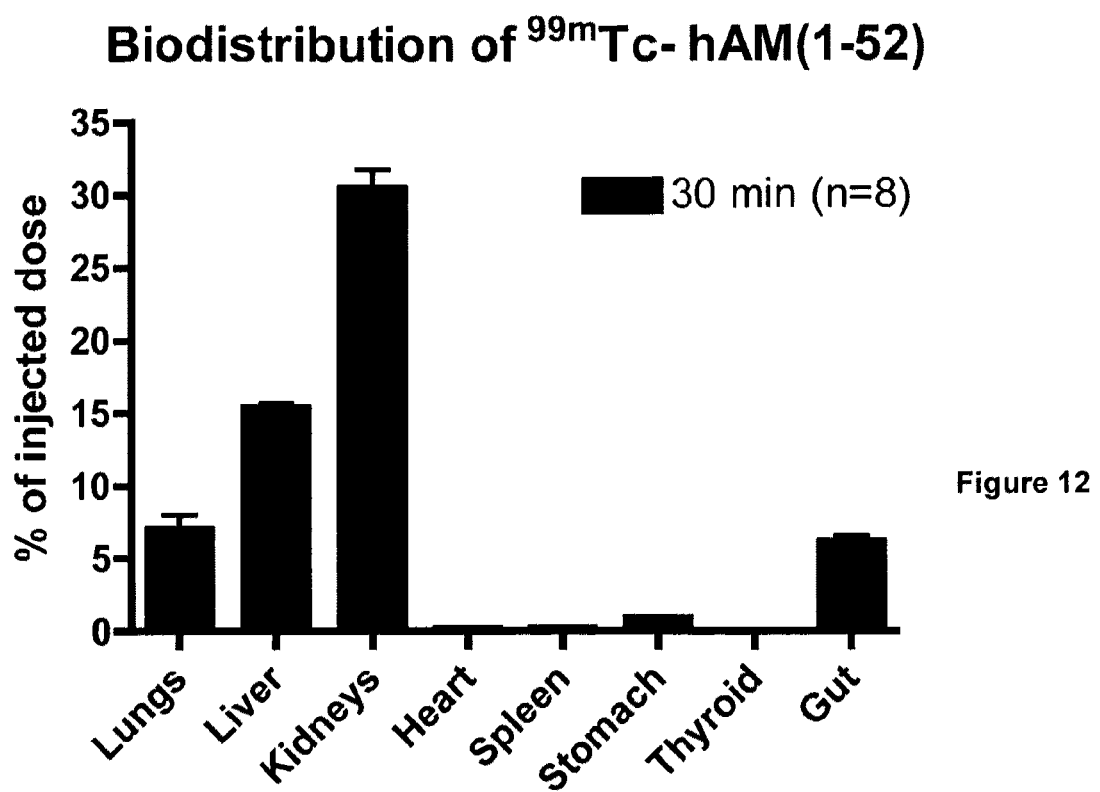
FIG. 12, in a bar chart, illustrates the biodistribution in various organs of $^{99m}$Tc-linear AM 30 minutes after intravenous injection in rats.
Figure 13:
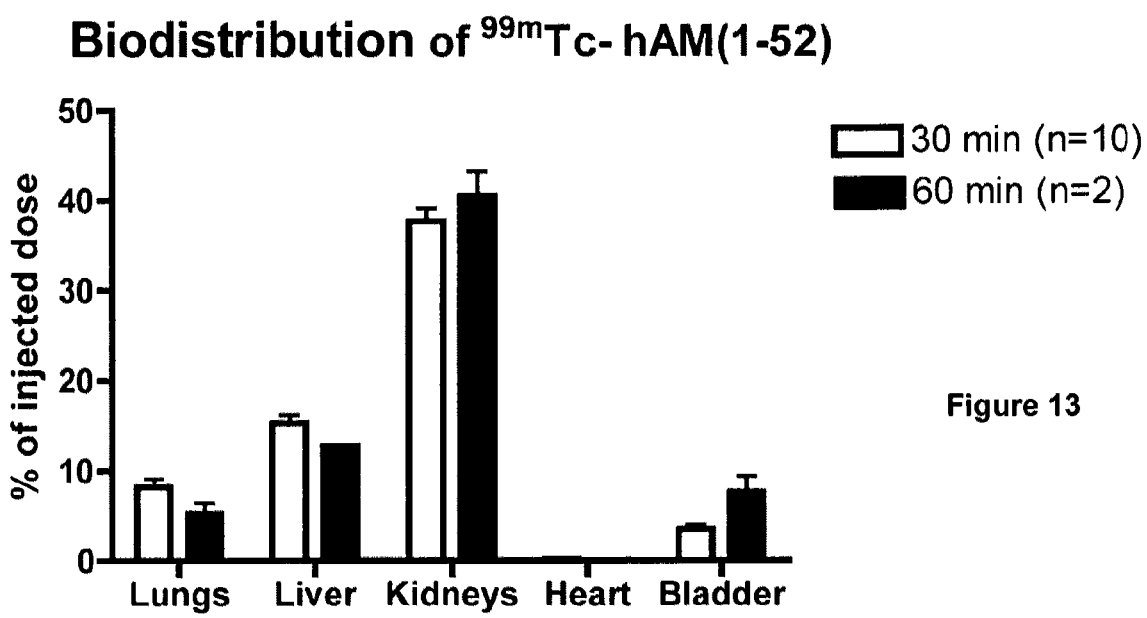
FIG. 13, in a bar chart, illustrates the biodistribution in various organs of $^{99m}$Tc-linear AM 30 and 60 minutes after intravenous injection in rats.

As seen in FIGS. 12 and 13, which illustrate the biodistribution of $^{99m}$Tc-AM in rats for various organs, $^{99m}$Tc-linear AM is significantly retained by lungs, the lung uptake being maintained for at least 1 hour, thereby enabling external imaging. $^{99m}$Tc-linear AM is eliminated by the kidneys (mostly) and the liver. Furthermore, thyroid uptake was minimal, which indicates that this compound is likely to be relatively safe for human use.

Figure 14:
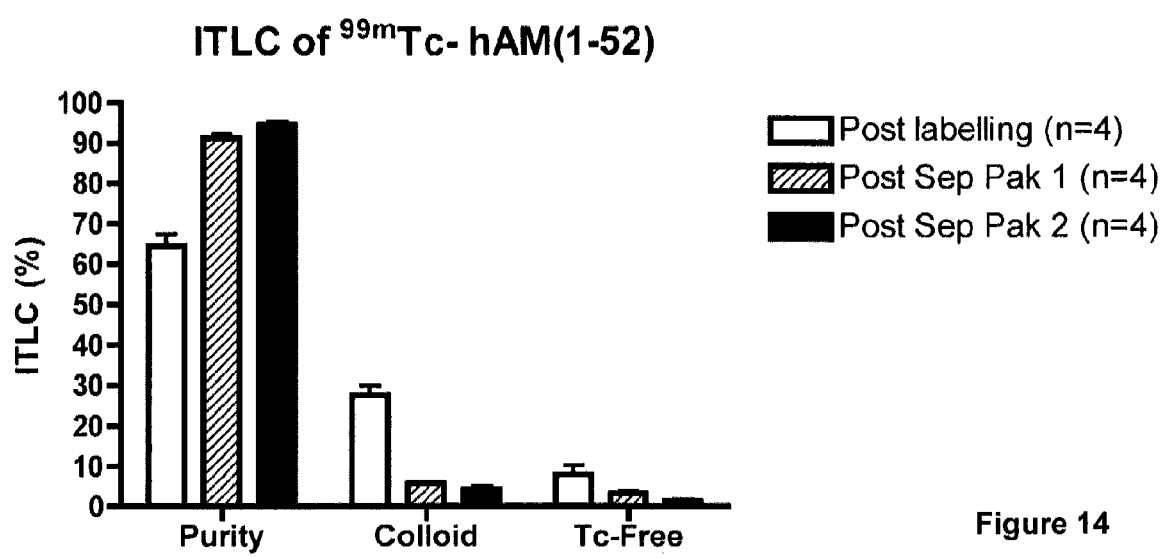
FIG. 14, in a bar chart, illustrates the purification of $^{99m}$Tc-linear AM using Sep Pak cartridges. The labelled compound is separated from colloids and free $^{99m}$Tc by instant thin layer chromatography (ITLC). After a first and second pass on a column, purified fractions of 91% and 94% respectively are obtained. This level of purification is suitable for in vivo utilization.

As seen in FIG. 14, labeling efficiency of purified $^{99m}$Tc linear hAM1-52 enabling potential human use can be obtained by mini-column purification. To evaluate amount of purified $^{99m}$Tc linear hAM1-52, colloids and unlabelled $^{99m}$Tc, instant thin layer chromatography on silica gel impregnated glass fiber paper (ITLC SG) (P/N 61886, Pall Life Sciences) was performed on 1) radiolabelled solution before mini-column purification, and 2) sample obtained after C18 mini-column purification. ITLC SG solvents were acetone (Fisher Scientific) for dosage of unlabelled 99mTc, and BAPE solution (30 U butanol; 6 U acetic acid; 24 U pyridine; 20 U nanopure water) for colloids evaluation. The $^{99m}$Tc linear hAM1-52 migrated only with the BAPE mixture. $^{99m}$Tc activity was assessed using an automatic gamma counter (model 1272 Clinigamma, LKB Wallac, Finland). Average radiochemical purity (% of 99mTc-DTPA-hAM1-52) was 65% prior to column separation, compared to 91% after a first column purification and 94% after a second column purification. For all experiments greater than 90% purification was used.

Figure 15:
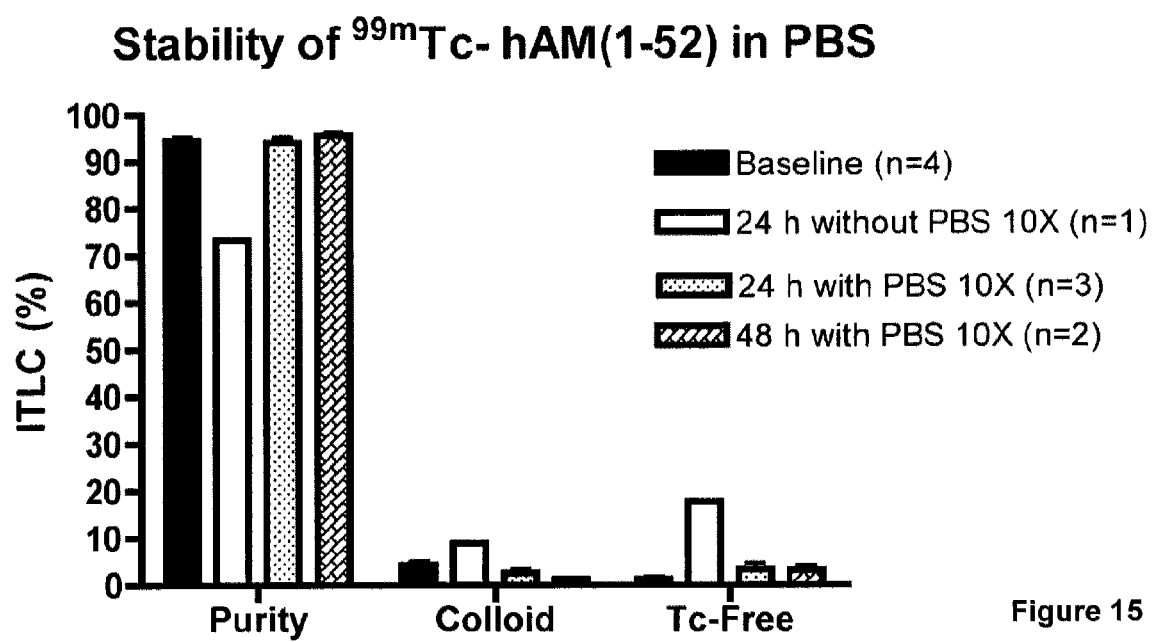
FIG. 15, in a bar chart, illustrates the stability of purified $^{99m}$Tc-linear AM at room temperature over periods of 24 and 48 hours as assessed by instant thin layer chromatography (ITLC). In a solution of phosphate buffered saline (PBS) the purified compound is stable and maintains radiochemical purity of 94% for up to 48 hours.

FIG. 15 illustrates the stability of purified $^{99m}$Tc linear hAM1-52 at room temperature as verified by ITLC after 24 and 48 hours. The product is stable and retains greater than 90% purity after 48 hours in phosphate buffered saline (PBS). Such stability is important and desirable as product for clinical imaging may require delay between preparation and injection.

Figure 16:
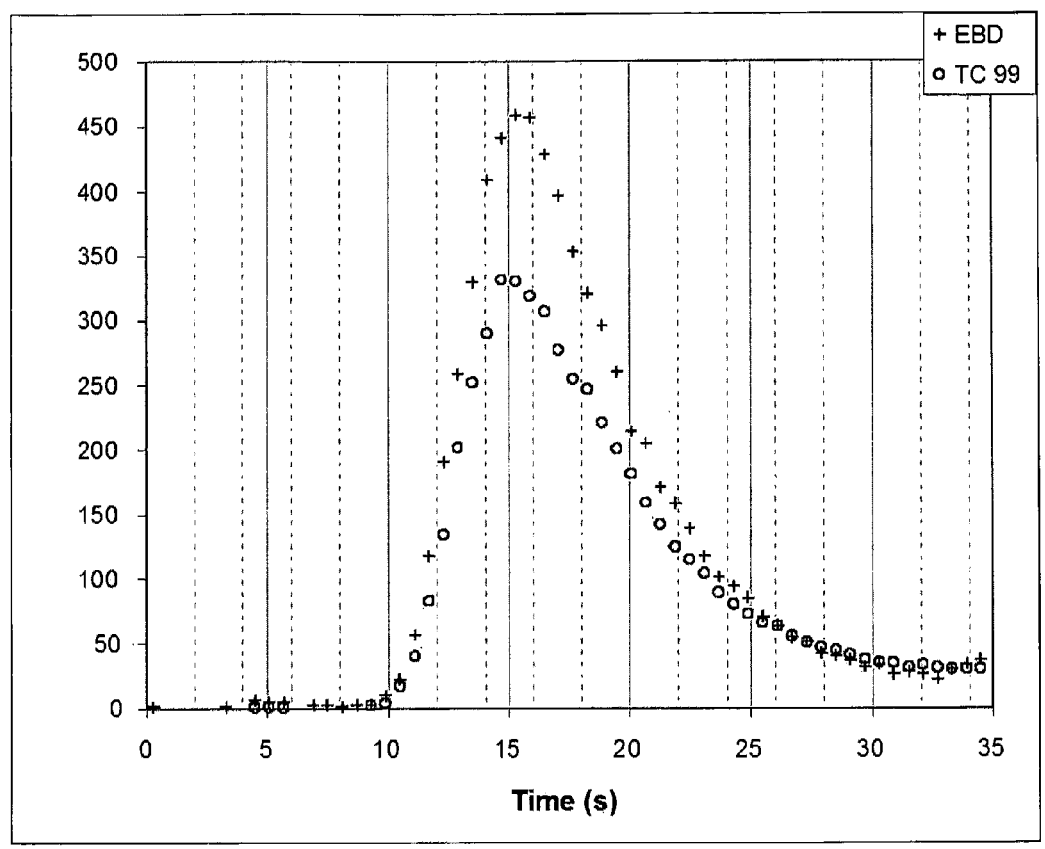
FIG. 16, in a X-Y graph, illustrates an example of a first pass pulmonary clearance experiment of $^{99m}$Tc-linear AM in a dog in vivo. A bolus containing trace amounts of $^{99m}$Tc-linear AM (TC99) and Evans blue dye labelled albumin (EBD) are injected in the pulmonary artery and timed outflow samples are collected over 35 seconds. The concentration in each sample is plotted as a function of time to construct and indicator-dilution curve. The differential area between the curves represents mean tracer $^{99m}$Tc-linear AM extraction within a single pulmonary passage. In this example, mean extraction was 21%.

FIG. 16 illustrates in vivo single-pass measurement of purified $^{99m}$Tc linear hAM1-52 clearance in dogs. Dogs were anesthetized and a catheter was inserted into the carotid artery and positioned just above the aortic valve. This catheter is connected to a peristaltic pump for automated blood withdrawal. Another catheter is placed into the jugular vein and positioned in the right ventricular outflow tract to allow bolus injection of the study tracers. A bolus was prepared by adding 2 mCi of purified $^{99m}$Tc linear hAM1-52 to 3 ml of Evans blue dye labeled albumin and 0.9% saline for a final volume of 6 ml. A single bolus indicator-dilution experiment was performed. The collected samples were processed and indicator-dilution curves constructed and analysed. Mean tracer $^{99m}$Tc linear hAM1-52 AM extraction during the pulmonary transit time was computed from the curves. Mean tracer extraction corresponds to the difference between the areas of the outflow curve of the vascular reference (albumin) and that of the extracted tracer ($^{99m}$Tc linear hAM1-52). Recirculation of the tracers apparent in the terminal portion of the curves is removed by linear extrapolation of the semi-logarithmic down slopes.

FIG. 16 demonstrates significant single pass extraction of purified $^{99m}$Tc linear hAM1-52 by the dog lung with a mean extraction of 21% in this example.

EXAMPLE 7

Affinity of Various Human Adrenomedullin (hAM) Derivatives with the Lungs

Figure 17A:
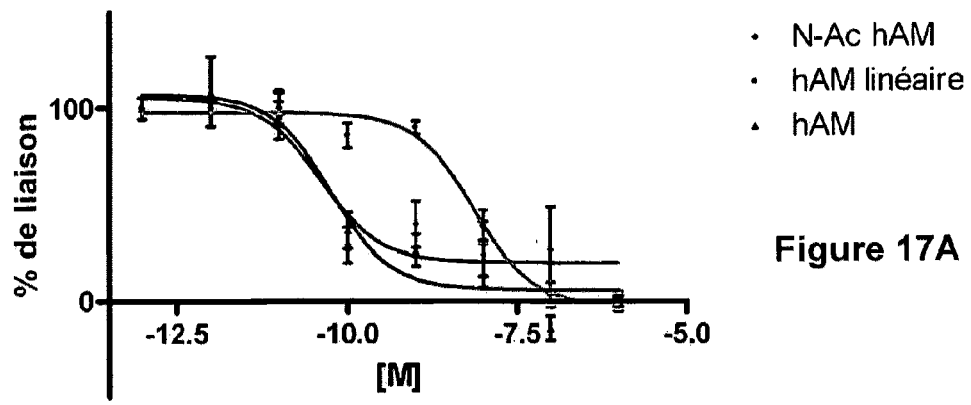
FIGS. 17A, 17B and 17C, in X-Y graphs, illustrate the displacement of $^{99m}$TC marked cyclic AM by various $^{99m}$TC marked AM derivatives as a function of concentration of the $^{99m}$TC marked AM variants time-dependent biodistribution.
Figure 17B:
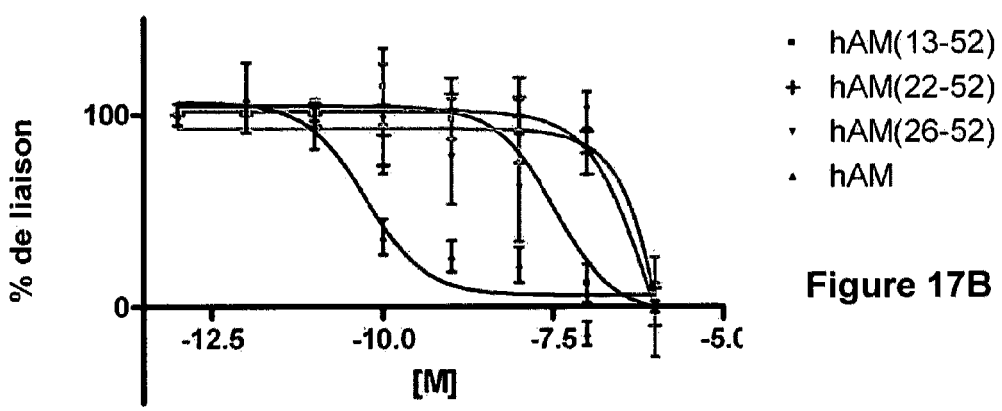
Figure 17C:
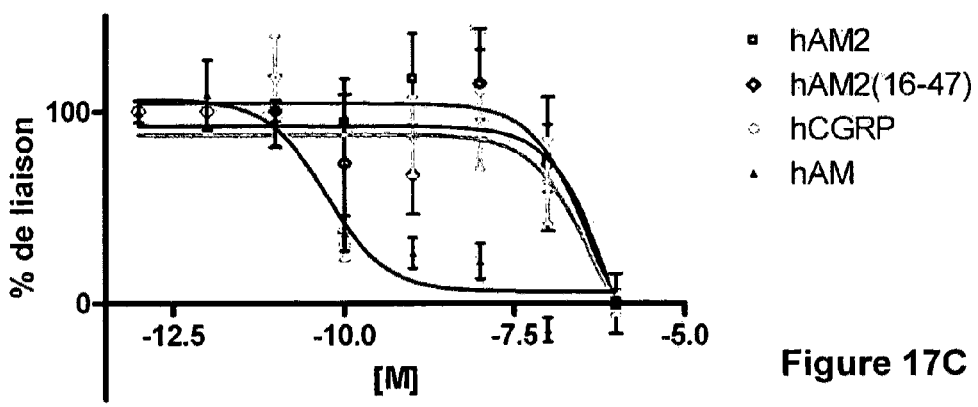

FIGS. 17A, 17B and 17C illustrate the capability of various human adrenomedullin (hAM) derivatives (amino acids contained in each fragment mentioned in parenthesis) in displacing iodine-marked human adrenomedullin in the lungs of dogs. These Figures illustrate that there is clearly a relatively well-defined concentration of the different peptides that allow to displace 50% of the human adrenomedullin in the lungs. These concentrations, denoted by IC-50, are shown in Table 1 for various adrenomedullin fragments and linear and cyclic adrenomedullin peptides.

TABLE 1

IC$_{50}$ of various adrenomedullin derivatives.

| Synthetic Peptides | IC$_{50}$ |
|---|---|
| hAM (cyclic) | $5.5 \times 10^{-11}$ M |
| hAM linear | $7.1 \times 10^{-9}$ M |
| N-Ac hAM | $4.1 \times 10^{-11}$ M |
| hAM(1-25) | $\geq 10^{-5}$ M |
| hAM(13-52) | $3.4 \times 10^{-8}$ M |
| hAM(22-52) | $8.1 \times 10^{-7}$ M |
| hAM(26-52) | $\geq 10^{-6}$ M |
| hAM(40-52) | $\geq 10^{-5}$ M |
| hAM2 | $4.8 \times 10^{-7}$ M |
| hAM2(16-47) | $9.8 \times 10^{-7}$ M |
| hCGRP | $4.4 \times 10^{-7}$ M |
| CGRP(8-37) | $\geq 10^{-5}$ M |
| PAMP | $\geq 10^{-5}$ M |

Table 1 clearly shows that linear adrenomedullin (hAM linear) binds relatively well to the receptors to which cyclic adrenomedullin binds in the lungs of dogs. Indeed, the IC-50 of linear hAM is only two orders of magnitude larger than the IC-50 of cyclic hAM. Therefore, linear adrenomedullin, which is relatively easily synthesized and allows to bind some radioactive elements thereto, such as $^{99M}$Tc, may be used in lung imagery for various applications.

N-terminal acetylated AM (N-Ac hAM) did not seem to affect the binding of hAM to the lungs of dogs. Also, the results from these binding experiments of peptides from the CT family correspond to the binding profile for the AM1 (CRLR+RAMP2) receptor: AM>AM (13-52)>CGRP and AM (22-52)>CGRP (8-37).

AM2, a peptide within the same family as AM has an affinity similar to CGRP for the lung of dogs. It is likely that AM2 binds to a complex including CRLR and another RAMP protein.

In addition, binding of L-AM and C-AM was evaluated by using a human breast adenocarcinoma cell line (MCF-7). These cells express approximately 50,000 AM receptors per cell. For each peptide, competition binding experiments were performed in triplicates using $^{125}$I-AM(1-52). Both C-AM and L-AM displayed competitive binding on MCF-7 cells with IC50 of 19.6 nM and 70.3 nM respectively.

EXAMPLE 8

Imaging of the Lungs with Purified $^{99m}$Tc Linear hAM1-52

Figure 18:
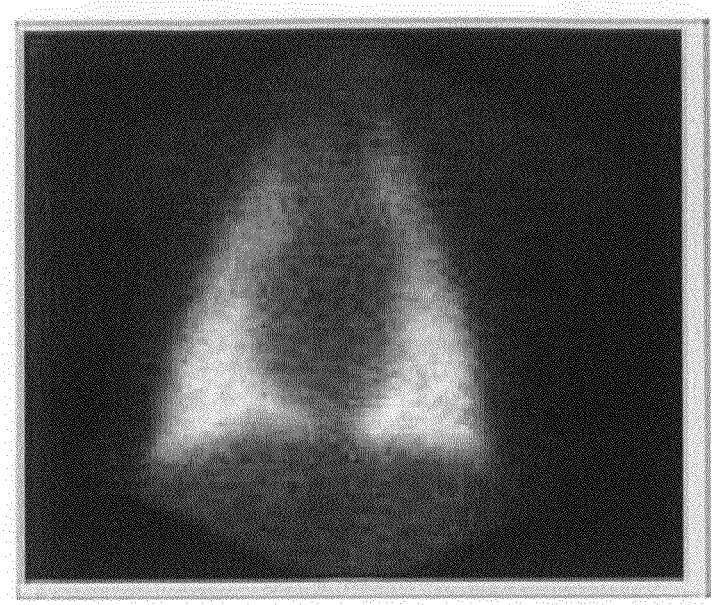
FIG. 18 is a gamma camera image of a dog's thorax obtained further to an injection of $^{99m}$TC marked linear AM showing a substantially homogeneous lung uptake of the tracer, thereby enabling external imaging.
Figure 19:
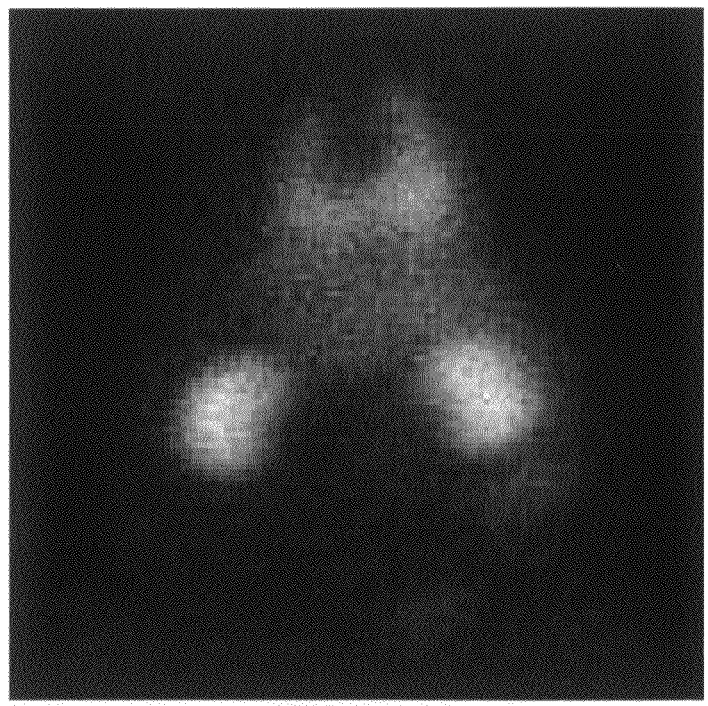
FIG. 19 is a gamma camera image of a mouse's thorax and abdomen obtained further to an injection of $^{99m}$TC marked linear AM showing a substantially homogeneous lung uptake of the tracer, thereby enabling external imaging.

FIGS. 18 and 19 illustrate respectively images of the lungs of a dog and a rat to which purified $^{99m}$Tc linear hAM1-52 has been administered. In both species there is relatively specific and homogeneous pulmonary uptake, thereby enabling good external imaging.

EXAMPLE 9

Bio-Distribution of Cyclic and Linear $^{99m}$Tc-AM in Dogs

The bio-distribution of cyclic and linear $^{99m}$Tc-AM was studied in dogs as a function of time in various organs. Cyclic or linear $^{99m}$Tc-AM was injected in dogs and multi-organic biodistribution of 99mTc-DTPA-hAM1-52 was evaluated with a gamma camera. Following intravenous injection, dynamic acquisition of the lungs, heart, liver and kidneys was recorded for a 30-min period (one frame/sec during the first minute, then one frame/min for the remaining time). Static acquisitions was also recorded for whole individual organs, including lungs, kidneys, liver, heart, bladder, gallbladder and muzzle, at 30, 60, 120, 240 minutes after initial injection. These recordings were performed both in ventral and dorsal positions. Dynamic and static acquisitions were evaluated by using Matlab version 7.01 image analysis tools software. The $^{99m}$Tc total count, $^{99m}$Tc mean count, and region of interest (ROI) size were calculated for each organ. Data correction was applied for 1) radioactive decay, 2) table correction (dorsal images only), 3) geometric mean, and 4) organ's attenuation based on transmission factor. Results were expressed as a percentage of total radioactivity injected.

As seen from FIG. 20, cyclic and linear $^{99m}$Tc AM binds relatively selectively to the kidneys with between 20 and 30% retention and are only slowly eliminated from this organ as this amount of retention is maintained at 120 min. These results are surprising as linear adrenomedullin is the equivalent of a denatured protein and it could be expected that such a derivative of adrenomedullin could only weakly bind to adrenomedullin specific receptors in any of the organs studied in this experiment. Therefore, these results suggest that not only cyclic but also labeled linear adrenomedullin and derivative thereof have a potential to be useful in the imaging of the lungs.

EXAMPLE 10

Plasma Kinetics of $^{99m}$Tc-Cyclic AM and $^{99m}$Tc-Linear AM

The plasma kinetics of $^{99m}$Tc-cyclic AM and $^{99m}$Tc-linear AM were studied in 7 and 6 dogs respectively. The radiolabelled AM derivatives were injected in a volume of 1.5 mL into a right jugular vein catheter. A series of 200 μl blood samples were collected 1 min after the initial injection, then repeated every 5 min for a 30-min period. After each collection, an equal volume of saline was injected into the animal to maintain blood volume and pressure. The blood samples were then placed in a gamma counter (model 1470 Wizard, Wallac, Finland) to determine $^{99m}$Tc activity. Results were expressed as a percentage of total radioactivity injected.

Figure 21:
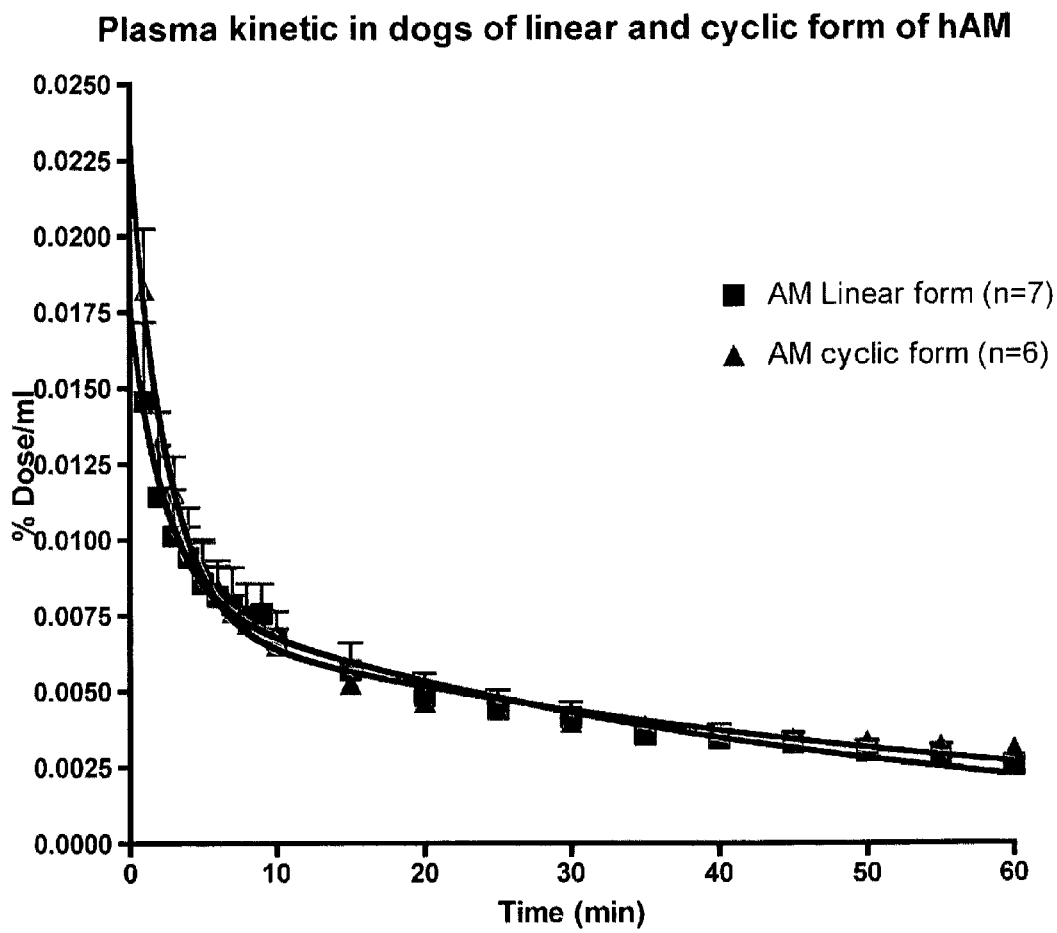
FIG. 21, in a X-Y graph, illustrates the plasma kinetics of $^{99m}$Tc-cyclic hAM and $^{99m}$Tc-linear human AM (hAM) after a single intravenous injection in dogs.

As seen from FIG. 21, $^{99m}$Tc-cyclic and $^{99m}$Tc-linear AM are cleared relatively rapidly from the plasma. The data illustrated in FIG. 21 was used to determine the parameters of two-compartment model, which gave a relatively rapid distribution half-life of less than two min and an elimination half-life of less than 45 minutes for both derivatives.

Figure 22:
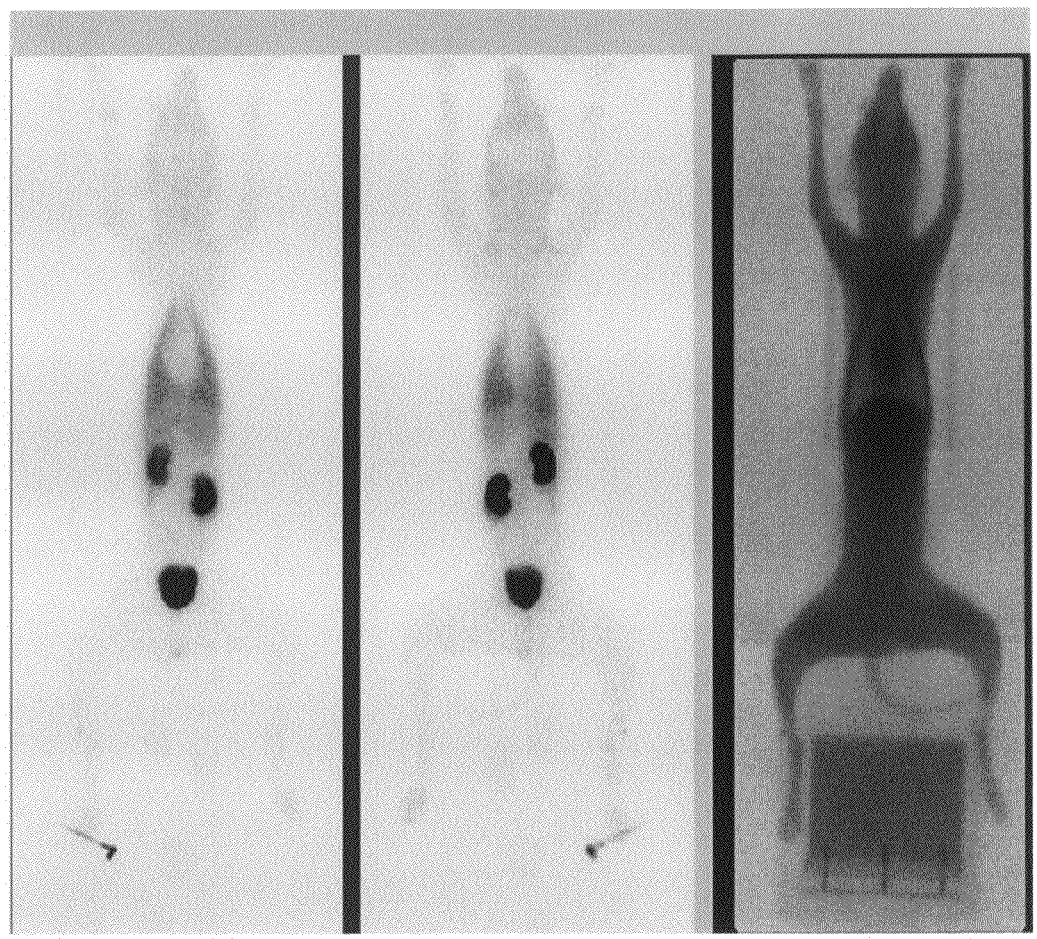
FIG. 22 is a whole body gamma camera image of a dog obtained further to an injection of $^{99m}$TC marked linear AM. There is homogeneous kidney uptake of the tracer enabling external imaging.

As seen in FIG. 22 which illustrates whole body imaging of $^{99m}$Tc-linear AM in a dog 120 min after injection, $^{99m}$Tc-linear AM is significantly retained by the kidney enabling good quality external imaging. The images were acquired using a Siemens dual hear Ecam Gamma camera 120 min after injection of the compound. Anterior and posterior views are seen on the left and center while an attenuation image (similar to an x-ray) is demonstrated on the left. It is also notable that urinary bladder activity is also easily seen as the tracer is excreted by the kidneys.

Figure 23:
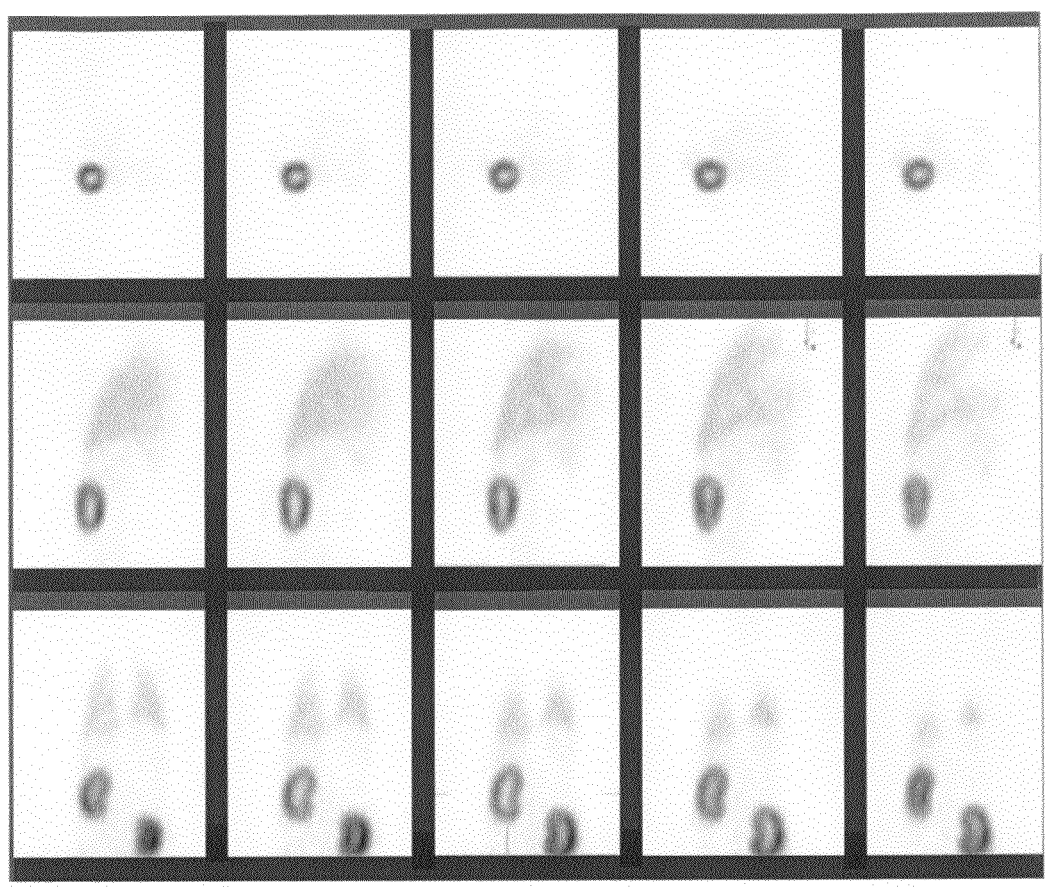
FIG. 23 represent tomographic gamma camera images of dog kidneys obtained further to an injection of $^{99m}$TC marked linear AM in transverse, sagittal and coronal sections. There is homogeneous kidney uptake of the tracer that is limited to the kidney cortex enabling external imaging.

FIG. 23 illustrates tomographic slices of the kidney from the same animal in transverse (first row), sagittal (middle row) and frontal sections (bottom row). $^{99m}$Tc-linear AM is seen to concentrate in the kidney cortex, the kidney medulla being free of activity. This confirms that the distribution of AM binding sites are located at the kidney cortex and that the tracer could specifically be used to image conditions known to affect cortical kidney function.

EXAMPLE 11

Kidney Imaging

Kidney damage was induced by a single intraperitoenal injection of monocrotaline 60 mg/kg in rats. Three weeks later the animal received were anaesthetized and mechanically ventilated. An intravenous injection of 800 μci $^{99m}$Tc-linear AM was performed by the jugular vein and received and intravenous and 30 minutes later the activity retained by the kidneys was determined by two different approaches: first by external imaging using a dual-hear Siemens Ecam gamma camera by drawing regions of interest around the kidneys, and second, after the animals were sacrificed and their kidneys removed and counted in a gamma counter to determine $^{99m}$Tc activity. By both methods, the activity in the kidneys was expressed as a percentage of the total activity injected.

Figure 24:
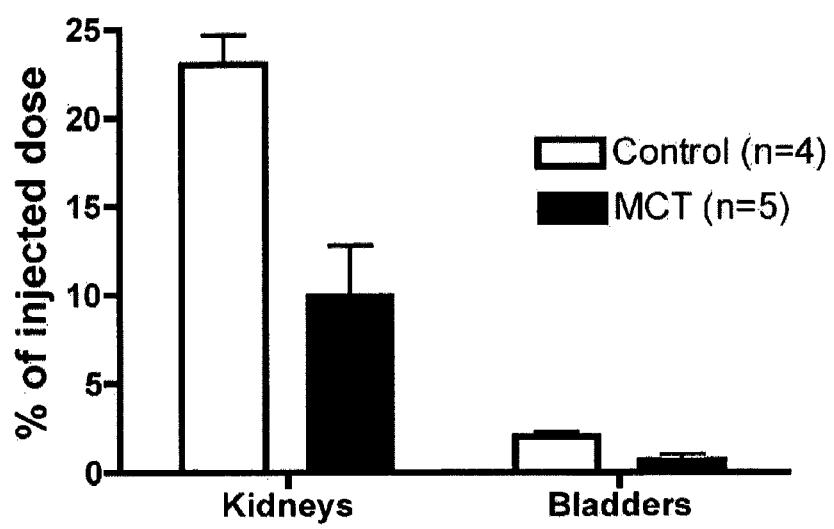
FIG. 24 represents kidney and bladder uptake of $^{99m}$TC marked linear AM further to injection to control rats and to rats with kidney damage induces by monocrotaline injection (MCT). There is more than 50% reduction in relative kidney uptake after MCT suggesting that this agent could be used in the diagnosis of kidney disorders.

FIG. 24 is a bar chart representing kidney activity in control rats (n=4) and in monocrotaline treated rats (n=5) after 3 weeks after kidney injury using external detection by an Ecam. Kidney uptake of the tracer was reduced by more than half form 23%±3% to 10%±6% after monocrotaline injury. This was concordant with the external counting of the organs (27%±6% and 11%±7% respectively). The use of labelled AM derivatives therefore allows for the detection of kidney damage in this animal model, and in other subjects, for example by integrating the detected radioactivity over a kidney obtained by imaging the kidney in a subject in which radioactively labelled AM or AM derivative has been injected and comparing this integrated radioactivity with a baseline radioactivity obtainable in healthy subjects.

EXAMPLE 12

Imaging of Pulmonary Arterial Hypertension

AM-L Synthesis and Purification

Linear adrenomedullin (AM-L) was synthesized using a solid phase procedure based on a fluorenylmethyloxycarbonyl (Fmoc) chemistry with a Rink-AM-amide resin (Chem-Impex International, Ill., USA) as the solid support. N-α-Fmoc protected amino acids (Matrix Innovation Inc., QC, Canada) were introduced in the peptide chain following a benzotriazol-1-yl-oxy-tris(dimethylamino)-phosphonium hexafluorophosphate (BOP) coupling strategy and each coupling reaction was monitored to confirm its completion. Cleavage from the solid support to obtain crude peptide was achieved with a mixture of trifluoroacetic acid (TFA)/ethanedithiol/water (92.5:2.5:2.5; 20 ml/g). After TFA evaporation, the peptide was precipitated using diethylether.

AM-L was purified by reversed phase-HPLC (RP-HPLC) using a Flanged MODCOL column (25×3.5 cm) packed with a Jupiter C18 matrix (15 μm, 300 Å) (Phenomenex, Calif., USA). The purification step was carried out using a Varian ProStar system at a flow rate maintained at 20 ml/min. The UV-Vis detector was set at 220 nm and the peptide was eluted from the column with a 2 h gradient from 10% to 50% ACN/H2O containing 0.06% TFA.

The purity of the collected fractions was evaluated through analytical RP-HPLC and the mass was established with MALDI-TOF mass spectrometry (Voyager DE, Applied Biosystems, Calif., USA). Homogeneous fractions corresponding to the desired peptide were then pooled and aliquoted in 2.9 nmol samples, before lyophilization.

Radiolabelling and Purification

Sample vials containing 2.9 nmol AM-L were kept at −20° C. Radiolabelling was performed by adding to the vial 100 μL of HCl 1 mM, and 14.8 µL of SnCl2.2H$_2$O (0.2 mg/mL-13 nmol). Immediately after dissolving the material, 15 mCi of freshly prepared Na$^{99m}$TcO$_4$ (28.9 pmol) in saline solution was added and the mixture was kept at room temperature for 1 h. Following the radiolabelling step, 1 mL of PBS (pH 7.4) was added to the solution.

The totality of the $^{99m}$Tc-AM-L reaction mixture was injected onto a 1 cc (100 mg) C18 Sep-Pak cartridge. The cartridge was then washed with 3 mL of 1 mM hydrochloric acid and eluted with 3 mL of a 50% ethanol solution. Fractions of 0.5 mL were collected into sterile polypropylene tubes. Fractions and cartridge radioactivity count was then measured and three fractions with the highest counts were pooled. 200 µL of 10× sterile PBS (pH 7.4) was added and the radiochemical purity measured by instant thin layer chromatography using ITLC-SG strips from PALL Life Sciences (PALL Corp.) was 95%.

Studies in Monocrotaline (MCT)-Induced Pulmonary Arterial Hypertension

Male Sprague Dawley rats weighting between 200-225 g received an 0.5 mL intraperitoneal (IP) injection of either 0.9% saline or 60 mg/kg monocrotaline (MCT). Five weeks later, rats were anesthetized for hemodynamic measurements using Millar microtip pressure transducer catheters.

Nuclear Medicine Experiments.

The animals were anesthetized by an initial intra-muscular dose of xylazine (10 mg/kg) and ketamine (50 mg/kg), followed by an intraperitoneal injection of heparin (2000 U, Sigma Chemical Co.). Additional doses of xylazine/ketamine were used if noxious stimuli (hind feet pinching) could elicit nociceptive motor reflexes or changes of the systemic blood pressure.

99mTc-AM-L was injected in a volume of 200 µl (0.3 pmol, 0.5 mCi) into the right jugular vein. A series of 200 µl blood samples were collected 1 and 3 min after the initial AM injection, then repeated every 5 min for a 30-min period. After each sample collection, an equal volume of saline was injected into the animal to maintain blood volume and pressure.

The whole body biodistribution of radiolabelled peptide was evaluated using two different approaches: in vivo by imaging with a gamma camera system, and ex vivo by surgically removing and counting organs in a gamma counter. In vivo multi-organic biodistribution of $^{99m}$Tc-AM-L was evaluated with a Siemens E.Cam signature camera system equipped with on board computer, and a low-energy parallel-hole collimator. Following intravenous injection of $^{99m}$Tc-AM-L, dynamic acquisition was recorded for a 30-min period (one frame/sec during the first minute, then one frame/min for the remaining time). Static acquisitions were also recorded for whole individual organs, including lungs, kidneys, liver, heart and bladder at 30 minutes after initial injection. At the end of in vivo acquisition, the animals were sacrificed and the lungs, liver, kidneys and heart (separated into right ventricle, left ventricle+septum) were removed, gravity drained and weighted. The blood samples and organs were then placed in a gamma counter (model 1470 Wizard, Wallac, Finland) to determine $^{99m}$Tc activity. Results were expressed as a percentage of total radioactivity injected.

Molecular Biology Experiments.

To perform lung protein extraction, the snap frozen right inferior lobe was homogenized using a polytron homogenizer in lysis buffer containing a protease inhibitor cocktail. The homogenate was clarified by centrifugation and the final protein concentration was determined. Fifty micrograms of protein per sample were separated on a 15% SDS-PAGE gel for 1 hour at 200V at 40 C and transferred onto a polyvinylidene difluoride membrane at 100V for 90 min at 40 C. The membrane was subsequently blocked for 2 hours at room temperature with 5% skimmed milk powder in PBS 1× and 0.01% tween 20 (PBS-T) and incubated overnight at 40 C with primary rabbit polyclonal antibody raised against amino acids 28-166 of RAMP2 of human origin (Santa Cruz). The antibody was diluted 1:500 with 5% milk in PBS-T overnight at 40 C. The membrane was then washed with PBS-T and re-blocked for 10 min with 5% milk diluted in PBS-T. The membrane was then incubated with the appropriate horseradish peroxiduse-conjugated secondary antibody for rabbit (Jackson Laboratories) diluted 1:10000 in 5% milk PBS-T. Following three washes, the immunoreactive bands were visualized by enhanced chemiluminescence (Renaissance Plus, Perkin Elmer Life Sciences) according to the manufacturer's instruction using Bio-Max MR film. Anti-Actin 1:1000 antibody was used as the housekeeping gene.

Statistical Analysis

Differences between groups were evaluated by two-tailed independent samples t-tests. Plasma kinetics of $^{99m}$Tc-AM-L were analyzed using a two compartments pharmacokinetic model with Prism v4.0 software and the fitted curves were compared using an F test. All values are reported as means±standard deviations.

Results

MCT rats developed severe PAH with right ventricular systolic pressure of 88±26 mmHg (n=11) compared to 30±7 mmHg (n=8) in controls, P<0.001. There was also important right ventricular hypertrophy evidenced by higher right to left ventricular+septum weight ratio of 0.50±0.07 compared to 0.22±0.07, P<0.001.

Figure 25:
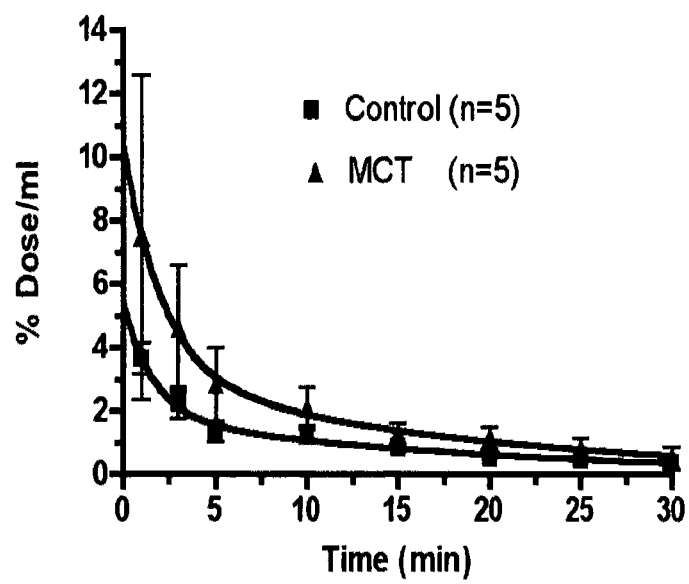
FIG. 25 illustrates the plasma kinetics of $^{99m}$TC marked linear AM in a control group and in a monocrotaline-induced pulmonary arterial hypertension (PAH) (MCT) group. The fitted two-compartment model curves are significantly different with p<0.001.

Plasma kinetics of $^{99m}$Tc-AM-L are presented in FIG. 25. The fitted curves were significantly different (P<0.001) with plasma levels approximately two-fold higher in PAH compared to control animals. After 10 minutes, levels were 1.25±0.28% the injected dose (ID) in controls compared to 2.08±0.65% ID in PAH animals (P=0.03).

Figure 26:
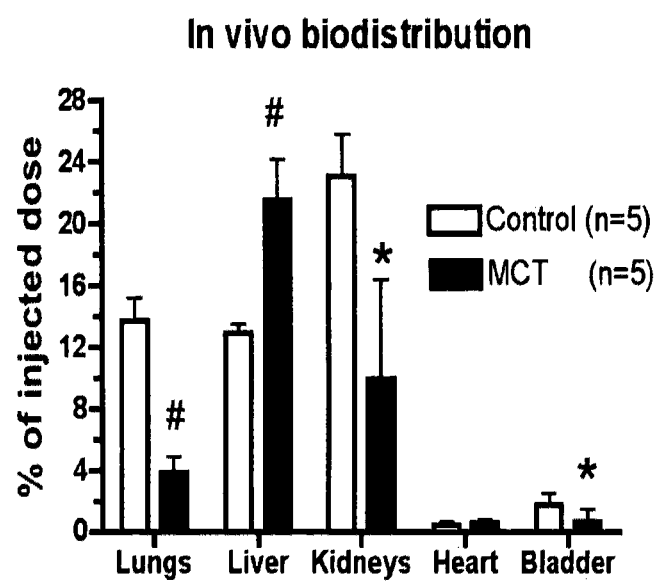
FIG. 26 illustrates in vivo biodistribution of $^{99m}$TC marked linear AM in the control group and in the monocrotaline-induced PAH (MCT) group. # p<0.001 versus control, * p<0.05 versus control.
Figure 27:
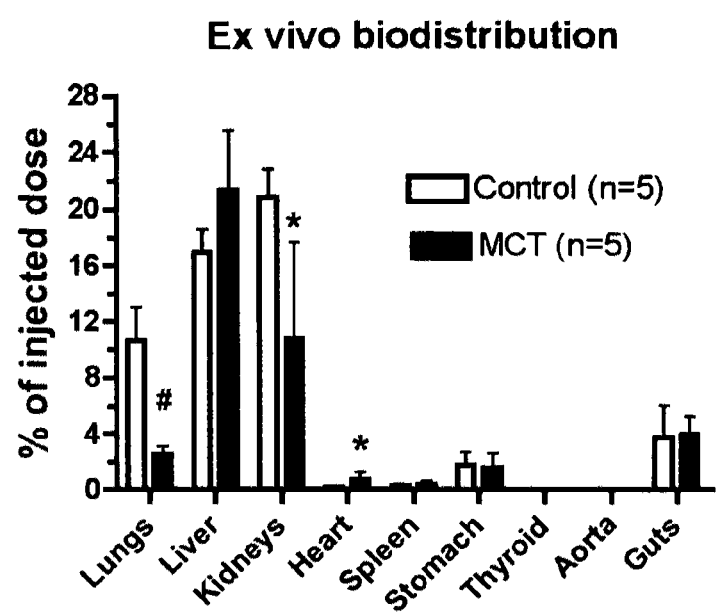
FIG. 27 illustrates ex vivo biodistribution of $^{99m}$TC marked linear AM in the control group and in the monocrotaline-induced PAH (MCT) group. # p<0.001 versus control, * p<0.05 versus control.

The biodistribution of $^{99m}$Tc-AM-L 30 minutes after injection was determined by two different approaches: in vivo by using a gamma camera (FIG. 26) and ex vivo by counting the explanted organs in a gamma counter (FIG. 27). The in vivo biodistribution revealed a markedly reduced lung uptake of the tracer from 14±1% ID in controls to 4±1% in PAH, P<0.0001. A similar retention and reduction was observed ex vivo with 11±2% ID vs. 3±1%, P<0.001. The MCT treated group also demonstrated increased liver uptake but lower kidney and bladder activities compared to the control group. Interestingly, although the heart displayed very little retention of this molecular imaging agent, the uptake as measured ex vivo was increased in the PAH animals from 0.18±0.03% ID to 0.77±0.46% ID, P=0.02. The increased uptake in the right heart ventricle correlated with RV weight (r=0.83, P<0.01) while there was no correlation for the left ventricle+septum (r=−0.58).

Figure 28:
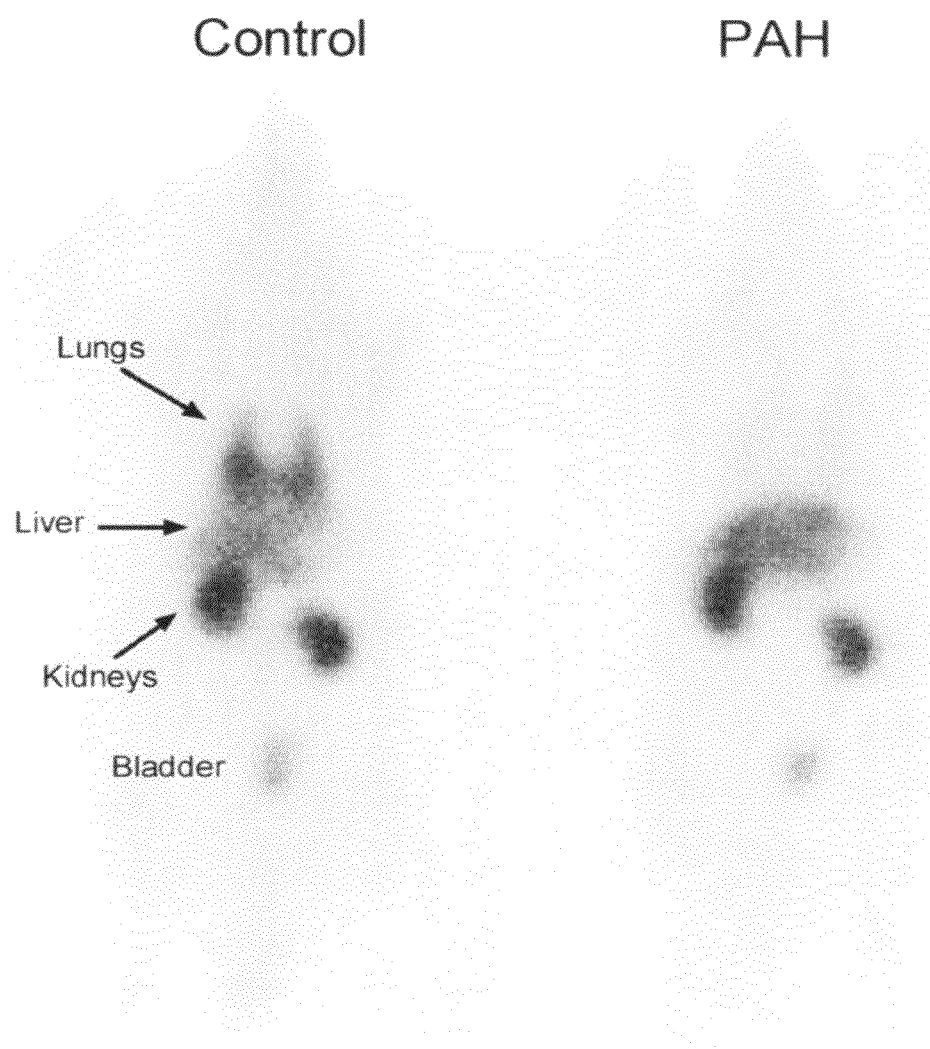
FIG. 28 illustrates whole body scans 30 minutes following intravenous 99mTc-AM-L injection. A) control animal B) PAH model animal.

Whole body images of rats 30 minutes after injection are presented in FIG. 28. There is homogeneous bilateral lung uptake in control rats with marked reduction of $^{99m}$Tc-AM-L in the animals with PAH as there is barely any visibly evident lung uptake.

Figure 29:
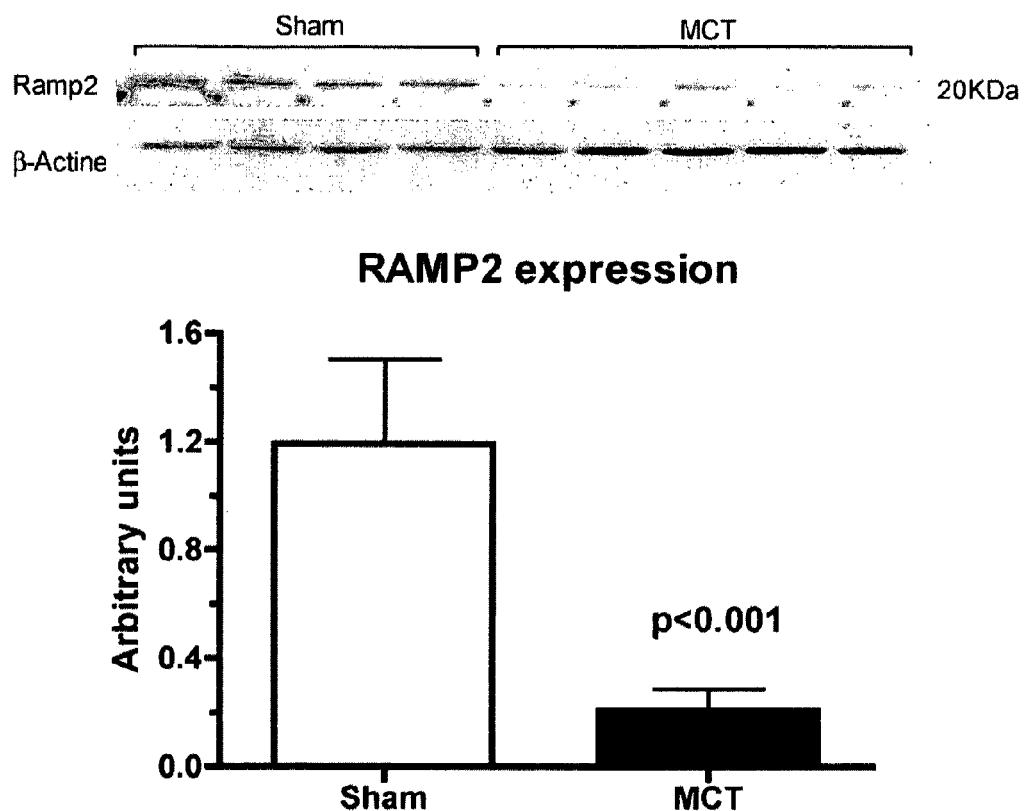
FIG. 29 illustrates lung tissue protein expression of the AM receptor component RAM P2 in Sham and MCT treated rats.

The heterodimeric AM receptor component, receptor activity modifying protein 2 (RAMP2), was evalutated in lung tissue by western immunoblots. There was marked reduction of RAMP2 protein expression (FIG. 29) in PAH rats (P<0.001).

Discussion

A linear human AM derivative radiolabelled with $^{99m}$Tc was used for imaging of the pulmonary circulation and tested its ability to diagnose PAH. It was demonstrated that a molecular imaging agent can be used to detect abnormalities of the pulmonary microcirculation. In PAH, lung uptake of $^{99m}$Tc-AM-L was markedly reduced.

PAH is a disorder characterized by medial hypertrophy of pulmonary arterioles with intimal proliferation leading to obliteration and loss of pulmonary circulation. There currently exists no test that can non-invasively detect this loss of pulmonary micro-circulation. The MCT model of PAH, although lacking the intimal proliferation of human PAH, is similarly associated with medial hypertrophy with obliteration and loss of pulmonary arterioles [41, 42]. The observed reduction in $^{99m}$Tc-AM-L uptake in PAH could therefore in great part be caused by reduced pulmonary vascular surface with loss of AM receptors. However, other mechanisms could be involved without limiting the scope of the present invention.

The AM receptor is a heterodimeric G-protein coupled receptor composed of two components, the calcitonin receptor like receptor (CLR) and a receptor activity modifying protein (RAMP2) [43]. Large-scale analysis of the human and mouse transcriptomes revealed that RAMP2 is relatively equally distributed among most tissues, with the notable exception of very high expression levels in the lungs (44). Human and rat lungs indeed contain a high density of specific AM binding sites (39, 40) mostly distributed on the vascular endothelium. This is concordant with studies demonstrating that the lung is an important site for circulating AM clearance [37, 38]. Acute lung injury in a sepsis model is associated with markedly increased circulating AM levels with concomitant 95% reduction in lung RAMP2 expression, suggesting that reduced lung binding and clearance could contribute to the increased plasma levels [45]. In the current study, we also evaluated lung RAMP2 protein expression and found that it was markedly reduced by about 80%. This is consistent with the approximate 70% reduction in lung uptake that we found and with the increased (doubling) of plasma 99mTc-AM-L levels in PAH.

An interesting and unexpected finding was the increase in the heart uptake of $^{99m}$Tc-AM-L in PAH that correlated with the severity of right ventricular hypertrophy. Although the expression of AM receptors was not evaluated in the RV, this would suggest that AM receptors are present and that their expression is increased by RVH. Whether increased uptake by the RV could be detected clinically and serve as an index of RVH would require further validation but this would certainly provide useful additional information.

The MCT model of lung injury with PAH is not selective to the pulmonary circulation. Another organ sensitive to the effect of MCT is the kidney and previous studies have used MCT injection as a model of renal injury [46]. Although this study was not specifically designed to evaluate kidney function, we found that MCT resulted in reduced kidney uptake of $^{99m}$Tc-AM-L by about 50%. This suggests that loss of kidney AM uptake could be used to evaluate kidney damage in this model but further studies specifically evaluating the kidneys AM system in this model and others.

EXAMPLE 13

Additional Derivatives and Their Clinical Properties

FIG. 30 illustrates in table form and summarizes some of the salient features of additional experiments with various AM derivatives. In this table, the "base" AM is hAM as identified in SEQ ID NO: 01. The sequences of these derivatives are depicted by comparison to human cyclic AM (the first listed). Through novel modifications in the peptides, we have created new compounds that have potential clinical advantages. Various AM derivatives that were investigated for different properties. These derivatives were synthesized as follows.

All adrenomedullin (AM) analogs were synthesized through solid phase peptide synthesis following a standard procedure for Fmoc chemistry. A Rink AM resin was chosen as the solid support. Amino acids were incorporated to the peptide chain in accordance with the AM(21-52) sequence of the natural peptide. In cases in which PEG subunits are inserted, a Fmoc-dPEG$_2$-OH or Fmoc-dPEG$_4$-OH derivative was added to replace amino acids found between cysteine residues of the complete AM peptide while maintaining dimensions similar to those of the native peptide. The coupling protocol used for all amino acids was also followed for the PEG including AM derivatives. A cysteine residue was coupled onto the deprotected amine group of the PEG spacer and finally, the chelating moiety, if present and which corresponds in some examples to a 4-amino acid sequence, was attached to the peptide chain following the same peptide synthesis procedure. More details concerning methods usable for synthesizing such AM derivatives are found in previous examples.

By removing the 1-12 fragment of hAM, we demonstrate that the fragment 1-12 is not essential either for binding to the lung or for hemodynamic activity. Derivatives that have 13-52 morphology are sufficient.

Figure 31:
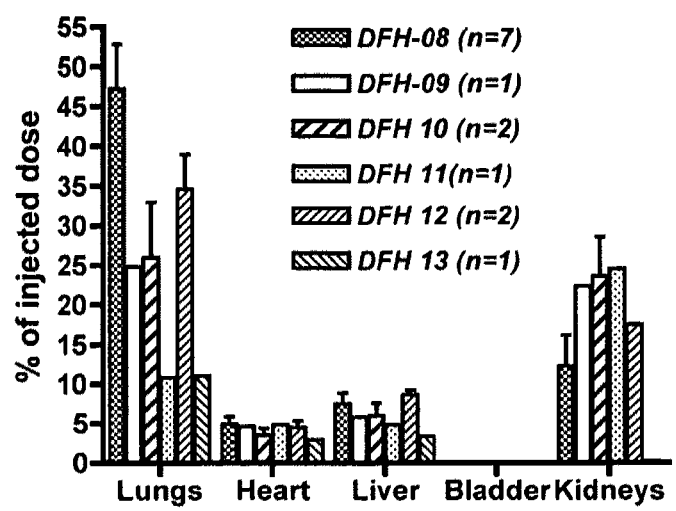
FIG. 31 illustrates the biodistribution of various AM derivatives radiolabelled with $^{99m}$Tc. The experiments were realized in vivo in dogs and the activity of each organ determined 30 minutes after injection using a gamma camera.
Figure 32:
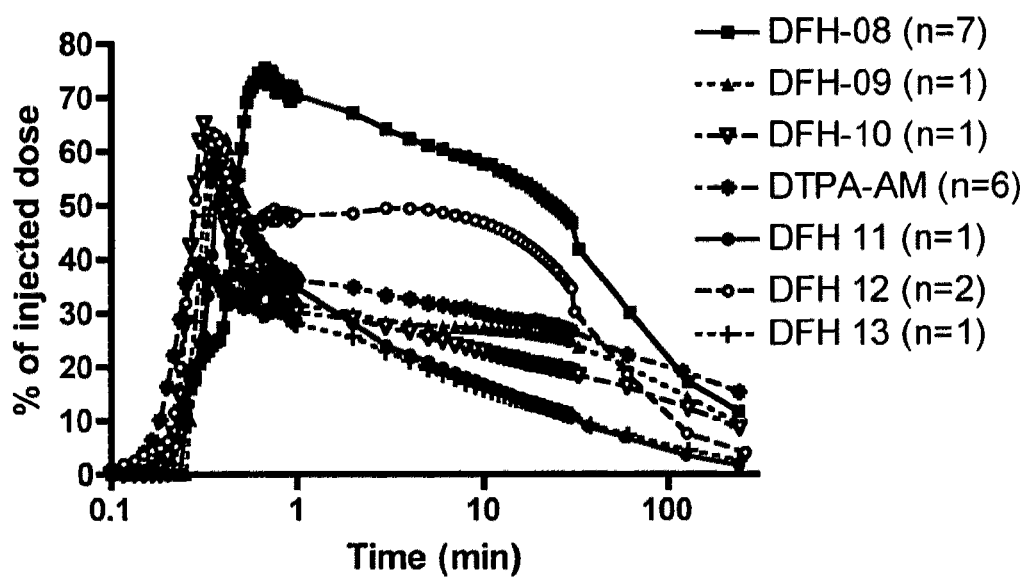
FIG. 32 illustrates the lung kinetics of AM derivatives in the first 120 minutes following injection in dogs. Of note is the plateau displayed by the AM derivative identified as DFH-12 in the table of FIG. 30 between 30 seconds and 45 minutes following injection.

This is seen by the data concerning the biodistribution of AM derivatives including and excluding these fragments in dogs after 30 min according to the protocols described hereinabove and illustrated in FIG. 31. These experiments establish that the presence of the two cysteine residues is important also for receptor binding (lung imaging) and for activity of the derivatives.

It was also established that by introducing a spacer between the two cysteine residues (polyethylene glycol, PEG2 and PEG4), good lung binding and imaging was obtained, but reduced unwanted hypotensive effects. Furthermore, replacement of the amino-acids in position 13,14 and 15 by the chelator Gly-Gly-dAla-Gly (GGAG) results in enhanced labelling of the tracer with Tc99M.

Furthermore, we demonstrate that the cyclic derivative with a spacer (PEG4) and the chelator GGAG provides the best lung kinetics using a protocol substantially similar to the protocols described hereinabove, as seen in FIG. 33, with a plateau effect as the tracer is retained in a more stable fashion by the lungs over 1 hour.

Although the present invention has been described hereinabove by way of preferred embodiments thereof, it can be modified, without departing from the spirit and nature of the subject invention as defined in the appended claims.

All references cited and/or discussed in this specification are incorporated herein by reference in their entirety and to the same extent as if each reference was individually incorporated by reference.

The in vivo experiments in rats and dogs, as described in the specification, may be predictive of biological effects in humans or other mammals and/or may serve as animal models for use of the present invention in humans or other mammals.

REFERENCES

1. Kitamura, K., Sakata, J., Kangawa, K., Kojima, M., Matsuo, H. and Eto, T. (1994) Cloning and characterization of 1. cDNA encoding a precursor for human adrenomedullin. Biochem. Biophys. Res. Commun. 194, 720-725
2. Sugo, S., Minamino, N., Kangawa, K. et al. (1994) Endothelial cells actively synthesize and secrete adrenomedullin. Biochem. Biophys. Res. Commun. 201, 1160-1166
3. Hinson, J. P., Kapas, S. and Smith, D. M. (2000) Adrenomedullin, a multifunctional regulatory peptide. Endocr. Rev. 21, 138-167
4. Hay, D. L. and Smith, D. M. (2001) Receptors: molecular identity and function. Peptides 22, 1753-1763
5. Kuwasako, K., Kitamura, K., Ito, K. et al. (2001) The seven amino acids of human RAMP2 (86) and RAMP3 (59) are critical for agonist binding to human adrenomedullin receptors. J. Biol. Chem. 276, 49459-49465
6. Poyner, D. R., Sexton, P. M., Marshall, I. et al. (2002) International Union of Pharmacology. XXXII. The mammalian calcitonin gene-related peptides, adrenomedullin, amylin, and calcitonin receptors. Pharmacol. Rev. 54, 233-246
7. Eguchi, S., Hirata, Y., Iwasaki, H. et al. (1994) Structure-activity relationship of adrenomedullin, a novel vasodilatory peptide, in cultured rat vascular smooth muscle cells. Endocrinolog 135, 2454-2458
8. Sabates, B., Granger, T., Choe, E. et al. (1996) Adrenomedullin is inactivated in the lungs of neonatal piglets. J. Pharm. Pharmacol. 48, 578-580
9. Hirayama, N., Kitamura, K., Imamura, T., Kato, J., Koiwaya, Y. and Eto, T. (1999) Secretion and clearance of the mature form of adrenomedullin in humans. Life Sci. 64, 2505-2509
10. Nishikimi, T., Kitamura, K., Saito, Y. et al. (1994) Clinical studies on the sites of production and clearance of circulating adrenomedullin in human subjects. Hypertension 24, 600-604
11. Nishikimi, T., Matsuoka, H., Shimada, K., Matsuo, H. and Kangawa, K. (2004) Production and clearance sites of two molecular forms of adrenomedullin in human plasma. Am. J. Hypertens. 13, 1032-1034
12. Nishikimi, T., Nagata, S., Sasaki, T. et al. (2001) The active molecular form of plasma adrenomedullin is extracted in the pulmonary circulation in patients with mitral stenosis: Possible role of adrenomedullin in pulmonary hypertension. Clin. Sci. 100, 61-66
13. Dupuis, J., Goresky, C. A. and Fournier, A. (1996) Pulmonary clearance of circulating endothelin-1 in dogs in vivo: Exclusive role of ETB receptors. J. Appl. Physiol. 81, 1510-1515
14. Kitamura, K., Kato, J., Kawamoto, M. et al. (1998) The intermediate form of glycine-extended adrenomedullin is the major circulating molecular form in human plasma. Biochem. Biophys. Res. Commun. 244, 551-555
15. Martinez, A., Miller, M. J., Catt, K. J. and Cuttitta, F. (1997) Adrenomedullin receptor expression in human lung and in pulmonary tumors. J. Histochem. Cytochem. 45, 159-164
16. Owji, A. A., Smith, D. M., Coppock, H. A. et al. (1995) An abundant and specific binding site for the novel vasodilator adrenomedullin in the rat. Endocrinology 136, 2127-2134
17. Poyner, D. R. (1997) Molecular pharmacology of receptors for calcitonin-gene-related peptide, amylin and adrenomedullin. Biochem. Soc. Trans. 25, 1032-1036
18. Dschietzig, T., Azad, H. A., Asswad, L., Bohme, C., Bartsch, C. and Baumann, G. (2002) The adrenomedullin receptor acts as clearance receptor in pulmonary circulation. Biochem. Biophys. Res. Commun. 294, 315-318
19. Qing, X., Svaren, J. and Keith, I. M. (2001) mRNA expression of novel CGRP1 receptors and their activity-modifying proteins in hypoxic rat lung. Am. J. Physiol. Lung Cell. Mol. Physiol. 280, L547-L554
20. Nagae, T., Mukoyama, M., Sugawara, A. et al. (2000) Rat receptor-activity-modifying proteins (RAMPs) for adrenomedullin/CGRP receptor: cloning and upregulation in obstructive nephropathy. Biochem. Biophys. Res. Commun. 270, 89-93
21. Hagner, S., Haberberger, R., Hay, D. L. et al. (2003) Immunohistochemical detection of the calcitonin receptor-like receptor protein in the microvasculature of rat endothelium. Eur. J. Pharmacol. 481, 147-151
22. Hagner, S., Stahl, U., Knoblauch, B., McGregor, G. P. and Lang, R. E. (2002) Calcitonin receptor-like receptor: identification and distribution in human peripheral tissues. Cell Tissue Res. 310, 41-50
23. Dilworth, J. R. and S. J. Parrott (1998). "The biomedical chemistry of technetium and rhenium." Chem. Soc. Rev. 27: 43-55.
24. Dupuis, J., A. Caron, et al. (2005). "Biodistribution, plasma kinetics and quantification of single pass pulmonary clearance of adrenomedullin." Clin Sci 1: 1.
25. Hinson, J. P., S. Kapas, et al. (2000). "Adrenomedullin, a multifunctional regulatory peptide." Endocr Rev 21(2): 138-67.
26. Hirayama, N., K. Kitamura, et al. (1999). "Secretion and clearance of the mature form of adrenomedullin in humans." Life Sci 64(26): 2505-9.
27. Hom, R. K. and J. A. Katzenellenbogen (1997). "Technetium-99m-labelled receptor-specific small-molecule radiopharmaceuticals: recent developments and encouraging results." Nucl Med Biol 24(6): 485-98.
28. Kitamura, K., J. Sakata, et al. (1993). "Cloning and characterization of cDNA encoding a precursor for human adrenomedullin." Biochem Biophys Res Commun 194(2): 720-5.
29. Liu, S. and D. S. Edwards (1999). "99mTc-Labelled Small Peptides as Diagnostic Radiopharmaceuticals." Chem Rev 99(9): 2235-68.
30. Nishikimi, T., K. Kitamura, et al. (1994). "Clinical studies on the sites of production and clearance of circulating adrenomedullin in human subjects." Hypertension 24(5): 600-4.
31. Nishikimi, T., H. Matsuoka, et al. (2000). "Production and clearance sites of two molecular forms of adrenomedullin in human plasma." Am J Hypertens 13(9): 1032-4.
32. Nishikimi, T., S. Nagata, et al. (2001). "The active molecular form of plasma adrenomedullin is extracted in the pulmonary circulation in patients with mitral stenosis: possible role of adrenomedullin in pulmonary hypertension." Clin Sci (Lond) 100(1): 61-6.
33. Schwochau, K. (2000). Technetium, Chemistry and Radiopharmaceutical Applications. Weinheim, Germany.
34. Sugo, S., N. Minamino, et al. (1994). "Endothelial cells actively synthesize and secrete adrenomedullin." Biochem Biophys Res Commun 201(3): 1160-6.
35. Forest, M. & Fournier, A.: BOP reagent for the coupling of pGlu and Boc His (Tos) in solid phase peptide synthesis. International Journal of Peptide and Protein Research, 1990; 35: 89-94
36. McLaughlin V V, McGoon M D. Pulmonary arterial hypertension. *Circulation* 2006; 114:1417-1431.
37. Dschietzig T, Azad H A, Asswad L, Bohme C, Bartsch C, Baumann G, Stangl K. The adrenomedullin receptor acts as clearance receptor in pulmonary circulation. *Biochem Biophys Res Commun* 2002; 294:315-318.

38. Dupuis J, Caron A, Ruel N. Biodistribution, plasma kinetics and quantification of single-pass pulmonary clearance of adrenomedullin. *Clin Sci* (*Lond*) 2005; 109:97-102.
39. Martinez A, Miller M J, Catt K J, Cuttitta F. Adrenomedullin receptor expression in human lung and in pulmonary tumors. *J Histochem Cytochem* 1997; 45:159-164.
40. Owji A A, Smith D M, Coppock H A, Morgan D G, Bhogal R, Ghatei M A, Bloom S R. An abundant and specific binding site for the novel vasodilator adrenomedullin in the rat. *Endocrinology* 1995; 136:2127-2134.
41. Reindel J F, Ganey P E, Wagner J G, Slocombe R F, Roth R A. Development of morphologic, hemodynamic, and biochemical changes in lungs of rats given monocrotaline pyrrole. *Toxicol Appl Pharmacol* 1990; 106:179-200.
42. Zhao Y D, Courtman D W, Deng Y, Kugathasan L, Zhang Q, Stewart D J. Rescue of monocrotaline-induced pulmonary arterial hypertension using bone marrow-derived endothelial-like progenitor cells: efficacy of combined cell and eNOS gene therapy in established disease. *Circ Res* 2005; 96:442-450.
43. Gibbons C, Dackor R, Dunworth W, Fritz-Six K, Caron K M. Receptor activity-modifying proteins: RAMPing up adrenomedullin signaling. *Mol Endocrinol* 2007; 21:783-796.
44. Su AI, Cooke M P, Ching K A, Hakak Y, Walker J R, Wiltshire T, Orth A P, Vega R G, Sapinoso L M, Moqrich A, Patapoutian A, Hampton G M, Schultz P G, Hogenesch J B. Large-scale analysis of the human and mouse transcriptomes. *Proc Natl Acad Sci USA* 2002; 99:4465-4470.
45. Ono Y, Okano I, Kojima M, Okada K, Kangawa K. Decreased gene expression of adrenomedullin receptor in mouse lungs during sepsis. *Biochem Biophys Res Commun* 2000; 271:197-202.
46. Kurozumi T, Tanaka K, Kido M, Shoyama Y. Monocrotaline-induced renal lesions. *Exp Mol Pathol* 1983; 39:377-386.
47. Yoshihara F, Nishikimi T, Okano I, Hino J, Horio T, Tokudome T, Suga S, Matsuoka H, Kangawa K, Kawano Y. Upregulation of intracardiac adrenomedullin and its receptor system in rats with volume overload-induced cardiac hypertrophy. *Regul Pept* 2005; 127:239-244.
48. Wang X, Nishikimi T, Akimoto K, Tadokoro K, Mori Y, Minamino N. Upregulation of ligand, receptor system, and amidating activity of adrenomedullin in left ventricular hypertrophy of severely hypertensive rats: effects of angiotensin-converting enzyme inhibitors and diuretic. *J Hypertens* 2003; 21:1171-1181.

What is claimed is:

1. A method of determining the presence and density of adrenomedullin receptor-bearing cells in a mammal comprising:

administering to the mammal an effective amount of labelled adrenomedullin derivative to achieve binding between the labelled adrenomedullin derivative and adrenomedullin-receptor-bearing cells; and imaging the mammal to determine distribution of the labelled adrenomedullin derivative;

the labelled adrenomedullin derivative comprising an adrenomedullin fragment having the sequence: X1-X2-

X3-X4-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr (SEQ ID NO:3), wherein:

X1 is absent or is selected from the group consisting of: Tyr-Arg-Gln-Ser-Met-Asn-Asn-Phe-Gln-Gly-Leu-Arg-Ser-Phe-Gly, Ser-Phe-Gly and Gly-Gly-Ala-Gly;

X2 is Cys or HomoCys;

when X1 is Ser-Phe-Gly or Gly-Gly-Ala-Gly, X3 is Arg-Phe-Gly-Thr or a linear or branched PEG moiety having at least two Poly(ethylene glycol) (PEG) subunits;

when X1 is absent or Tyr-Arg-Gln-Ser-Met-Asn-Asn-Phe-Gln-Gly-Leu-Arg-Ser-Phe-Gly, X3 is a linear or branched PEG moiety having at least two Poly(ethylene glycol) (PEG) subunits; and X4 is Cys or HomoCys.

2. The method of claim 1, wherein the adrenomedullin fragment is bound to a radioactive element.

* * * * *

SEQUENCE LISTING

```
<160> NUMBER OF SEQ ID NOS: 11

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 2
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 3
<211> LENGTH: 52
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(15)
<223> OTHER INFORMATION: This region may encompass "Tyr-Arg-Gln-Ser-Met-
      Asn-Asn-Phe-Gln-Gly-Leu-Arg-Ser-Phe-Gly", "Ser-Phe-Gly", "Gly-Gly-
      Ala-Gly" or not present
<220> FEATURE:
<221> NAME/KEY: MOD_RES
<222> LOCATION: (16)..(16)
<223> OTHER INFORMATION: Cys or HomoCys
<220> FEATURE:
<221> NAME/KEY: MOD_RES
<222> LOCATION: (17)..(20)
<223> OTHER INFORMATION: This region may or may not be present
<220> FEATURE:
<221> NAME/KEY: MOD_RES
<222> LOCATION: (21)..(21)
<223> OTHER INFORMATION: Cys or HomoCys
<220> FEATURE:
<223> OTHER INFORMATION: See specification as filed for detailed
      description of substitutions and preferred embodiments

<400> SEQUENCE: 3

Xaa Xaa Xaa Xaa Xaa Xaa Xaa Xaa Xaa Xaa Xaa Xaa Xaa Xaa Xaa Xaa
 1               5                  10                  15

Arg Phe Gly Thr Xaa Thr Val Gln Lys Leu Ala His Gln Ile Tyr Gln
                20                  25                  30

Phe Thr Asp Lys Asp Lys Asp Asn Val Ala Pro Arg Ser Lys Ile Ser
            35                  40                  45

Pro Gln Gly Tyr
    50

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Tyr Arg Gln Ser Met Asn Asn Phe Gln Gly Leu Arg Ser Phe Gly
 1               5                  10                  15

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Phe Gly
 1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Ala Gly
 1

<210> SEQ ID NO 7
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Phe Gly Thr
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: D-Ala

<400> SEQUENCE: 8

Gly Gly Ala Gly
  1

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Cys Arg Phe Gly Thr Cys
  1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ser Phe Gly Cys Arg Phe Gly Thr Cys
  1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ser Phe Gly Cys
  1
```